United States Patent
He et al.

(10) Patent No.: US 10,238,743 B2
(45) Date of Patent: Mar. 26, 2019

(54) C5-C6-FUSED TRICYCLIC IMINOTHIADIAZINE DIOXIDE COMPOUNDS AS BACE INHIBITORS, COMPOSITIONS, AND THEIR USE

(71) Applicants: Merck Sharp & Dohme Corp., Rahway, NJ (US); Shuwen He, Edison, NJ (US); Jared N. Cumming, Winchester, MA (US); Jack D. Scott, Scotch Plains, NJ (US)

(72) Inventors: Shuwen He, Edison, NJ (US); Jared N. Cumming, Winchester, MA (US); Jack D. Scott, Scotch Plains, NJ (US)

(73) Assignee: Merck Sharp & Dohme Corp.

(*) Notice: Subject to any disclaimer, the term of this patent is extended or adjusted under 35 U.S.C. 154(b) by 62 days.

(21) Appl. No.: 15/516,076

(22) PCT Filed: Sep. 28, 2015

(86) PCT No.: PCT/US2015/052554
§ 371 (c)(1),
(2) Date: Mar. 31, 2017

(87) PCT Pub. No.: WO2016/053828
PCT Pub. Date: Apr. 7, 2016

(65) Prior Publication Data
US 2017/0246300 A1  Aug. 31, 2017

Related U.S. Application Data

(60) Provisional application No. 62/059,631, filed on Oct. 3, 2014.

(51) Int. Cl.
| | |
|---|---|
| *A61K 45/06* | (2006.01) |
| *C07D 417/12* | (2006.01) |
| *C07D 471/04* | (2006.01) |
| *C07D 513/04* | (2006.01) |
| *C07D 519/00* | (2006.01) |
| *A61K 31/54* | (2006.01) |
| *A61K 31/549* | (2006.01) |
| *C07D 519/06* | (2006.01) |

(52) U.S. Cl.
CPC .............. *A61K 45/06* (2013.01); *A61K 31/54* (2013.01); *A61K 31/549* (2013.01); *C07D 417/12* (2013.01); *C07D 471/04* (2013.01); *C07D 513/04* (2013.01); *C07D 519/00* (2013.01); *C07D 519/06* (2013.01)

(58) Field of Classification Search
CPC ...... A61K 45/06; A61K 31/54; A61K 31/549; C07D 417/12; C07D 471/04; C07D 513/04; C07D 519/00; C07D 519/06
See application file for complete search history.

(56) References Cited

U.S. PATENT DOCUMENTS

| | | |
|---|---|---|
| 8,729,071 B2 | 5/2014 | Scott et al. |
| 8,940,748 B2 | 1/2015 | Scott et al. |
| 9,029,362 B2 | 5/2015 | Scott et al. |
| 9,221,839 B2 | 12/2015 | Cumming et al. |

(Continued)

FOREIGN PATENT DOCUMENTS

| | | |
|---|---|---|
| EP | 2855486 B1 | 4/2016 |
| WO | 2000037474 A1 | 6/2000 |

(Continued)

OTHER PUBLICATIONS

M.S. Malamas et al., 53 Journal of Medicinal Chemistry, 1146-1158 (2010).*
F. Yang et al., 280 The Journal of Biological Chemistry, 5892-5901 (2004).*
I. Hussain et al., 100 Journal of Neurochemistry, 902-809 (2007).*
D.A. Wolk et al., 65 Annals of Neurology, 557-568 (2009).*
I. Blasko et al., 29 Neurobiology of Aging, 1-11 (2008).*
A. Forsberg et al., 29 Neurobiology of Aging, 1456-1465 (2008).*
Abdel-Magid, 3 ACS Medicinal Chemistry Letters, 869-870 (2012).*
Barbiero et al., 182 Experimental Neurobiology, 335-345 (2003).*
D.J. Cook et al., 483 Nature 213-218 (2012).*
G. Tesco et al., 54 Neuron, 721-737 (2007).*

(Continued)

*Primary Examiner* — Alexander R Pagano
(74) *Attorney, Agent, or Firm* — Keith D. MacMillan; Catherine D. Fitch

(57) ABSTRACT

In its many embodiments, the present invention provides certain C5-C6 fused tricyclic iminothiadiazine compounds, including compounds Formula (I): or a tautomer thereof, and pharmaceutically acceptable salts of said compounds and said tautomers, wherein $R^{1,4}$, $R^2$, $R^3$, $R^A$, ring A, $R^A$, m, -$L_1$-, and $R^L$ are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including for the possible treatment of Alzheimer's disease, are also disclosed.

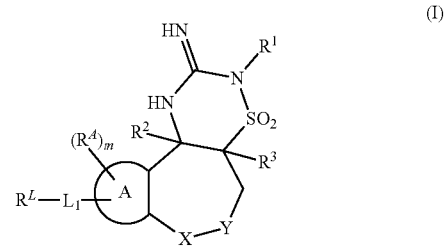

11 Claims, No Drawings

(56) References Cited

U.S. PATENT DOCUMENTS

| | | | |
|---|---|---|---|
| 9,365,589 B2 | 6/2016 | Cumming et al. |
| 9,428,475 B2 | 8/2016 | Scott et al. |
| 9,475,785 B2 | 10/2016 | Scott et al. |
| 9,580,396 B2 | 2/2017 | Cumming et al. |
| 2012/0189642 A1 | 7/2012 | Scott et al. |
| 2014/0023668 A1 | 1/2014 | Cumming et al. |
| 2016/0222032 A1 | 8/2016 | Scott et al. |
| 2016/0367563 A1 | 12/2016 | Scott et al. |

FOREIGN PATENT DOCUMENTS

| | | |
|---|---|---|
| WO | 2011044181 A1 | 4/2011 |
| WO | 2012162330 A1 | 11/2012 |
| WO | 2014093190 A1 | 6/2014 |
| WO | 2014099788 A1 | 6/2014 |
| WO | 2014099794 A1 | 6/2014 |
| WO | 2014120658 A1 | 8/2014 |
| WO | 2016085780 A1 | 6/2016 |

OTHER PUBLICATIONS

P.A. LeWitt, 359 New England Journal of Medicine, 2468-2473 (2008).*
S. Yamagishi et al., EC Neurology, 192-195 (2017).*
Y.S. Kim et al., 38 Experimental and Molecular Medicine, 333-347 (2006).*
International Search Report of PCT/US2015/052554 dated Dec. 17, 2015, 8 pages.

* cited by examiner

C5-C6-FUSED TRICYCLIC IMINOTHIADIAZINE DIOXIDE COMPOUNDS AS BACE INHIBITORS, COMPOSITIONS, AND THEIR USE

FIELD OF THE INVENTION

This invention provides certain C5-C6-fused tricyclic iminothiadiazine dioxide compounds, and compositions comprising these compounds, as inhibitors of BACE, which may be useful for treating or preventing pathologies related thereto, including, but not limited to, Alzheimer's disease.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making J-secretase a target for therapeutic intervention in AD. Ohno et al. Neurobiology of Disease, No. 26 (2007), 134-145, report that genetic deletion of BACE-1 in 5×FAD mice abrogates Aβ generation, blocks amyloid deposition, prevents neuron loss found in the cerebral cortex and subiculum (brain regions manifesting the most severe amyloidosis in 5×FAD mice), and rescues memory deficits in 5×FAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, certain groups have suggested the potential of BACE inhibition may be useful for traumatic brain injury. (Loane et al., "Amyloid precursor protein secretases as therapeutic targets for traumatic brain injury", Nature Medicine, 15, 377-379 (2009); Yu, et al., "Lithium reduces BACE1 overexpression, β amyloid accumulation, and spatial learning deficits in mice with traumatic brain injury", J Neurotrauma, 2012 September; 29(13): 2342-51; Tran, et al., "Controlled cortical impact traumatic brain injury in 3xTg-AD mice causes acute intra-axonal amyloid-β accumulation and independently accelerates the development of tau abnormalities", J Neurosci. 2011 Jun. 29; 31(26):9513-25). Still other diverse pathologies characterized by the inappropriate formation and deposition of Aβ or fragments thereof, and/or by the presence of amyloid fibrils, and/or for which inhibitor(s) of BACE are expected to be of therapeutic value are discussed further hereinbelow.

SUMMARY OF THE INVENTION

The present invention provides certain C5-C6-fused tricyclic iminothiadiazine dioxide compounds, which are collectively or individually referred to herein as "compound(s) of the invention," as described herein. The compounds of the invention are useful as inhibitors of BACE-1 and/or BACE-2.

In one embodiment, the compounds of the invention have the structural Formula (I):

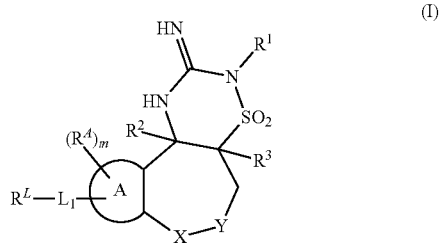

or a tautomer thereof having the structural Formula (I'):

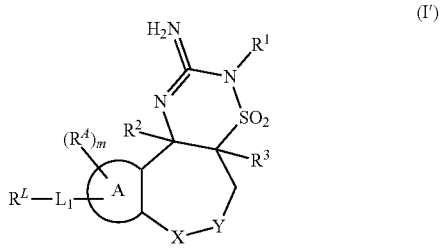

or pharmaceutically acceptable salt thereof, wherein:

-$L_1$- is a divalent moiety selected from the group consisting of —C(O)NH—, —CH$_2$C(O)NH—, —NH—, —CH(CH$_3$)NH— and —CH$_2$NH—;

$R^1$ is selected from the group consisting of H, alkyl, cycloalkyl, and -alkyl-cycloalkyl,
wherein each said alkyl, cycloalkyl, and -alkyl-cycloalkyl, is optionally substituted with one or more halogen, and
wherein 1 to 2 non-adjacent, non-terminal carbon atoms in said alkyl are optionally independently replaced with —O—, —NH—, —N(alkyl)-, —S—, —S(O)—, or —S(O)$_2$—;

$R^2$ is selected from the group consisting of H, alkyl, cycloalkyl, -alkyl-cycloalkyl, heterocycloalkyl, and -alkyl-heterocycloalkyl,
wherein each said alkyl, cycloalkyl, -alkyl-cycloalkyl, heterocycloalkyl, and -alkyl-heterocycloalkyl is optionally substituted with one or more halogen, and
wherein 1 to 2 non-adjacent, non-terminal carbon atoms in said alkyl are optionally independently replaced with —O—, —NH—, —N(alkyl)-, —S—, —S(O)—, or —S(O)$_2$—;

$R^3$ is selected from the group consisting of H, halogen, alkyl, cycloalkyl, and -alkyl-cycloalkyl,
wherein said alkyl, cycloalkyl, and -alkyl-cycloalkyl are optionally substituted with one or more fluorine, and
wherein 1 to 2 non-adjacent, non-terminal carbon atoms in said alkyl are optionally independently replaced with —O—, —NH—, or —N(alkyl)-;

X is selected from the group consisting of —C($R^{4X}$)$_2$—, —O—, —S—, —S(O)—, and —S(O)$_2$—, and Y is —C($R^{4Y}$)$_2$—,
or, alternatively, X is —C($R^{4X}$)$_2$— and Y is selected from the group consisting of —C($R^{4Y}$)$_2$—, —O—, —S—, —S(O)—, and —S(O)$_2$—;

each $R^{4X}$, when present, is independently selected from the group consisting of H, halogen, alkyl, and cycloalkyl,
wherein said alkyl and cycloalkyl are each optionally independently unsubstituted or substituted with one or more halogen, and
wherein 1 to 2 non-adjacent, non-terminal carbon atoms in said alkyl are optionally independently replaced with —O—, —NH—, —N(alkyl)-, —S—, —S(O)—, or —S(O)$_2$—;

each $R^{4Y}$, when present, is independently selected from the group consisting of H, halogen, alkyl, and cycloalkyl,
wherein said alkyl and cycloalkyl are each optionally independently unsubstituted or substituted with one or more halogen, and
wherein 1 to 2 non-adjacent, non-terminal carbon atoms in said alkyl are optionally independently replaced with —O—, —NH—, —N(alkyl)-, —S—, —S(O)—, or —S(O)$_2$—;

ring A is selected from the group consisting of aryl and heteroaryl;

m is 0 or more, with the proviso that the value of m does not exceed the number of available substitutable hydrogen atoms on ring A;

each $R^A$, when present, is independently selected from the group consisting of halogen, oxo, —OH, —CN, alkyl, —O-alkyl, and cycloalkyl,
wherein said alkyl, —O-alkyl, and cycloalkyl of $R^A$ are each optionally independently unsubstituted or substituted with one or more fluorine, and
wherein 1 to 2 non-adjacent, non-terminal carbon atoms in said alkyl are optionally independently replaced with —O—, —NH—, —N(alkyl)-, —S—, —S(O)—, or —S(O)$_2$—;

$R^L$ is selected from the group consisting of H and alkyl,
wherein said alkyl of $R^L$ are each optionally unsubstituted or substituted with one or more halogen, and
wherein 1 to 2 non-adjacent, non-terminal carbon atoms in said alkyl are optionally independently replaced with —O—, —NH—, —N(alkyl)-, —S—, —S(O)—, or —S(O)$_2$—;

or, alternatively, $R^L$ is a moiety having the formula

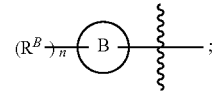

wherein
ring B is selected from the group consisting of aryl, heteroaryl, cycloalkyl, and heterocycloalkyl;
n is 0 or more, with the proviso that the value of n does not exceed the number of available substitutable hydrogen atoms on ring B; and each $R^B$, when present, is independently selected from the group consisting of halogen, oxo, —OH, —CN, —SF$_5$, —OSF$_5$, —OR$^{5B}$, —SR$^{5B}$, alkyl, alkenyl, alkynyl, cycloalkyl, -alkyl-cycloalkyl, heterocycloalkyl, -alkyl-heterocycloalkyl, aryl, and heteroaryl,
wherein said alkyl, alkenyl, alkynyl, cycloalkyl, -alkyl-cycloalkyl, heterocycloalkyl, -alkyl-heterocycloalkyl, aryl, and heteroaryl of $R^B$ are each optionally independently unsubstituted or substituted with one or more groups independently selected from $R^6$, and;
wherein 1 to 2 non-adjacent, non-terminal carbon atoms in said alkyl are optionally independently replaced with —O—, —NH—, —N(alkyl)-, —S—, —S(O)—, or —S(O)$_2$— each $R^{5B}$, when present, is independently selected from the group consisting of alkyl, alkenyl, alkynyl, cycloalkyl, -alkyl-cycloalkyl, heterocycloalkyl, -alkyl-heterocycloalkyl,
wherein each said alkyl, alkenyl, alkynyl, cycloalkyl, -alkyl-cycloalkyl, heterocycloalkyl, -alkyl-heterocycloalkyl of $R^{5B}$ is unsubstituted or optionally substituted with one or more fluorine, and
wherein 1 to 2 non-adjacent, non-terminal carbon atoms in said alkyl are optionally independently replaced with —O—, —NH—, —N(alkyl)-, —S—, —S(O)—, or —S(O)$_2$—; and each $R^6$, when present, is independently selected from the group consisting of halogen, —OH, —CN, alkyl, alkoxy, cycloalkyl, -alkyl-cycloalkyl, —O-cycloalkyl, heterocycloalkyl, and -alkyl-heterocycloalkyl,
wherein each said alkyl, alkoxy, cycloalkyl, -alkyl-cycloalkyl, —O-cycloalkyl, heterocycloalkyl, and -alkyl-heterocycloalkyl are optionally substituted with one or more fluorine, and
wherein 1 to 2 non-adjacent, non-terminal carbon atoms in said alkyl are optionally independently replaced with —O—, —NH—, —N(alkyl)-, —S—, —S(O)—, or —S(O)$_2$—.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s)

and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I) or (IA). In each of the embodiments described herein, each variable is selected independently of the other unless otherwise noted.

In one embodiment, the compounds of the invention have the structural Formula (IA):

(IA)

[chemical structure]

or a tautomer thereof having the structural Formula (IA'):

(IA')

[chemical structure]

or a pharmaceutically acceptable salt thereof, wherein each variable is as defined in Formula (I).

In one embodiment, in each of Formulas (I), (I'), (IA), and (IA'):
$R^1$ is selected from the group consisting of H, methyl, ethyl, cyclopropyl, —$CH_2$-cyclopropyl, and —$CH_2CH_2OCH_3$.

In one embodiment, in each of Formulas (I), (I'), (IA), and (IA'):
$R^1$ is selected from the group consisting of H and methyl.

In one embodiment, in each of Formulas (I), (I'), (IA), and (IA'):
$R^1$ is methyl.

In one embodiment, in each of Formulas (I), (I'), (IA), and (IA'):
$R^2$ is selected from the group consisting of H, methyl, ethyl, cyclopropyl, —$CH_2$-cyclopropyl, —$CH_2F$, —$CHF_2$, —$CF_3$, and —$CH_2OCH_3$.

In one embodiment, in each of Formulas (I), (I'), (IA), and (IA'):
$R^2$ is selected from the group consisting of methyl, cyclopropyl, and —$CHF_2$.

In one embodiment, in each of Formulas (I), (I'), (IA), and (IA'):
$R^2$ is methyl.

In one embodiment, in each of Formulas (I), (I'), (IA), and (IA'):
$R^3$ is selected from the group consisting of H, fluoro, methyl, ethyl, cyclopropyl, —$CH_2$-cyclopropyl, —$CH_2OCH_3$.

In one embodiment, in each of Formulas (I), (I'), (IA), and (IA'):
$R^3$ is selected from the group consisting of H, fluoro, and methyl.

In one embodiment, in each of Formulas (I), (I'), (IA), and (IA'):
$R^3$ is H.

In one embodiment, in each of Formulas (I), (I'), (IA), and (IA'):
$R^1$ is selected from the group consisting of H, methyl, ethyl, cyclopropyl, —$CH_2$-cyclopropyl, and —$CH_2CH_2OCH_3$;
$R^2$ is selected from the group consisting of H, methyl, ethyl, cyclopropyl, —$CH_2$-cyclopropyl, —$CH_2F$, —$CHF_2$, —$CF_3$, and —$CH_2OCH_3$; and
$R^3$ is selected from the group consisting of H, fluoro, chloro, methyl, ethyl, cyclopropyl, —$CH_2$-cyclopropyl, —$CH_2OCH_3$.

In one embodiment, in each of Formulas (I), (I'), (IA), and (IA'):
$R^1$ is selected from the group consisting of H and methyl;
$R^2$ is selected from the group consisting of methyl, cyclopropyl, and —$CHF_2$; and
$R^3$ is selected from the group consisting of H, fluoro, and methyl.

In one embodiment, in each of Formulas (I), (I'), (IA), and (IA'):
$R^1$ is methyl;
$R^2$ is methyl; and
$R^3$ is H.

In one embodiment, in each of Formulas (I), (I'), (IA), and (IA'):
X is selected from the group consisting of —$C(R^{4X})_2$— and —O—; and
Y is —$C(R^{4Y})_2$—.

In one embodiment, in each of Formulas (I), (I'), (IA), and (IA'):
X is —$C(R^{4X})_2$—; and
Y is selected from the group consisting of —$C(R^{4Y})_2$— and —O—.

In one embodiment, in each of Formulas (I), (I'), (IA), and (IA'):
X is —O—; and
Y is —$C(R^{4Y})_2$—.

In one embodiment, in each of Formulas (I), (I'), (IA), and (IA'):
X is —$C(R^{4X})_2$—; and
Y is —$C(R^{4Y})_2$—.

In one embodiment, in each of Formulas (I), (I'), (IA), and (IA'):

Each $R^{4X}$, when present, is independently selected from H, F, Me, and cyclopropyl.

In one embodiment, in each of Formulas (I), (I'), (IA), and (IA'):

$R^{4X}$, when present, is H.

In one embodiment, in each of Formulas (I), (I'), (IA), and (IA'):

Each $R^{4Y}$, when present, is independently selected from H, F, Me, and cyclopropyl.

In one embodiment, in each of Formulas (I), (I'), (IA), and (IA'):

$R^{4Y}$, when present, is H.

In one embodiment, in each of Formulas (I), (I'), (IA), and (IA'):

X is selected from the group consisting of —C($R^{4X}$)$_2$— and —O—;

Y is —C($R^{4Y}$)$_2$—;

each $R^{4X}$, when present, is independently selected from H, F, Me, and cyclopropyl; and each $R^{4Y}$ is independently selected from H, F, Me, and cyclopropyl with the proviso that when X is —O—, $R^{4Y}$ is not F.

In one embodiment, in each of Formulas (I), (I'), (IA), and (IA'):

X is —C($R^{4X}$)$_2$—;

Y is selected from the group consisting of —C($R^{4Y}$)$_2$— and —O—;

each $R^{4X}$ is independently selected from H, F, Me, and cyclopropyl with the proviso that when Y is —O—, $R^{4X}$ is not F; and each $R^{4Y}$, when present, is independently selected from H, F, Me, and cyclopropyl.

In one embodiment, in each of Formulas (I), (I'), (IA), and (IA'):

X is —O—;

Y is —C($R^{4Y}$)$_2$—; and each $R^{4Y}$ is independently selected from H, Me, and cyclopropyl.

In one embodiment, in each of Formulas (I), (I'), (IA), and (IA'):

X is —O—;

Y is —C($R^{4Y}$)$_2$—; and each $R^{4Y}$ is H.

In one embodiment, in each of Formulas (I), (I'), (IA), and (IA'):

X is —C($R^{4X}$)$_2$—;

Y is —C($R^{4Y}$)$_2$—;

each $R^{4X}$ is independently selected from H, F, Me, and cyclopropyl; and each $R^{4Y}$ is independently selected from H, F, Me, and cyclopropyl.

In one embodiment, in each of Formulas (I), (I'), (IA), and (IA'):

X is —C($R^{4X}$)$_2$—;

Y is —C($R^{4Y}$)$_2$—;

each $R^{4X}$ is H; and each $R^{4Y}$ is H.

The following alternative embodiments of ring A, $R^A$, and m are contemplated in combination with any of the embodiments described hereinabove.

In one embodiment, in each of Formulas (I), (I'), (IA), and (IA'):

ring A is selected from the group consisting of phenyl, pyridazinyl, pyridyl, pyrimidinyl, pyrazinyl, pyrazolyl, triazinyl, thiazolyl, and thienyl.

In an alternative of the immediately preceding embodiment, m is 0 or more, with the proviso that the value of m does not exceed the number of available substitutable hydrogen atoms on ring A; and each $R^A$ group, when present, is independently selected from the group consisting of fluoro, chloro, bromo, —CN, —OCH$_3$, —CH$_2$OCH$_3$, methyl, ethyl, cyclopropyl, —CF$_3$, —CHF$_2$, —CH$_2$F, —OCF$_3$, and —OCHF$_2$.

In one such alternative embodiment, m is 0, 1, 2, or 3. In another such alternative embodiment, m is 0, 1, or 2. In another such alternative embodiment, m is 0 or 1.

In another alternative of the immediately preceding embodiment, m is 0 or more, with the proviso that the value of m does not exceed the number of available substitutable hydrogen atoms on ring A; and each $R^A$, when present, is independently selected from the group consisting of fluoro, chloro, methyl, and —CHF$_2$.

In one such alternative embodiment, m is 0, 1, 2, or 3. In another such alternative embodiment, m is 0, 1, or 2. In another such alternative embodiment, m is 0 or 1.

In another alternative of the immediately preceding embodiment, m is 0 or more, with the proviso that the value of m does not exceed the number of available substitutable hydrogen atoms on ring A; and each $R^A$, when present, is fluoro.

In one such alternative embodiment, m is 0, 1, 2, or 3. In another such alternative embodiment, m is 0, 1, or 2. In another such alternative embodiment, m is 0 or 1.

In one embodiment, in each of Formulas (I), (I'), (IA), and (IA'):

ring A is selected from the group consisting of phenyl and pyridyl.

In an alternative of the immediately preceding embodiment, m is 0 or more, with the proviso that the value of m does not exceed the number of available substitutable hydrogen atoms on ring A; and each $R^A$ group, when present, is independently selected from the group consisting of fluoro, chloro, bromo, —CN, —OCH$_3$, —CH$_2$OCH$_3$, methyl, ethyl, cyclopropyl, —CF$_3$, —CHF$_2$, —CH$_2$F, —OCF$_3$, and —OCHF$_2$.

In one such alternative embodiment, m is 0, 1, 2, or 3. In another such alternative embodiment, m is 0, 1, or 2. In another such alternative embodiment, m is 0 or 1.

In another alternative of the immediately preceding embodiment, m is 0 or more, with the proviso that the value of m does not exceed the number of available substitutable hydrogen atoms on ring A; and each $R^A$, when present, is independently selected from the group consisting of fluoro, chloro, methyl, and —CHF$_2$.

In one such alternative embodiment, m is 0, 1, 2, or 3. In another such alternative embodiment, m is 0, 1, or 2. In another such alternative embodiment, m is 0 or 1.

In another alternative of the immediately preceding embodiment, m is 0 or more, with the proviso that the value of m does not exceed the number of available substitutable hydrogen atoms on ring A; and each $R^A$, when present, is fluoro.

In one such alternative embodiment, m is 0, 1, 2, or 3. In another such alternative embodiment, m is 0, 1, or 2. In another such alternative embodiment, m is 0 or 1.

In one embodiment, in each of Formulas (I), (I'), (IA), and (IA'):

ring A is phenyl.

In an alternative of the immediately preceding embodiment, m is 0 or more, with the proviso that the value of m does not exceed the number of available substitutable hydrogen atoms on ring A; and each $R^A$ group, when present, is independently selected from the group consisting of fluoro, chloro, bromo, —CN, —OCH$_3$, —CH$_2$OCH$_3$, methyl, ethyl, cyclopropyl, —CF$_3$, —CHF$_2$, —CH$_2$F, —OCF$_3$, and —OCHF$_2$.

In one such alternative embodiment, m is 0, 1, 2, or 3. In another such alternative embodiment, m is 0, 1, or 2. In another such alternative embodiment, m is 0 or 1.

In another alternative of the immediately preceding embodiment, m is 0 or more, with the proviso that the value of m does not exceed the number of available substitutable hydrogen atoms on ring A; and each $R^A$, when present, is independently selected from the group consisting of fluoro, chloro, methyl, and —CHF$_2$.

In one such alternative embodiment, m is 0, 1, 2, or 3. In another such alternative embodiment, m is 0, 1, or 2. In another such alternative embodiment, m is 0 or 1.

In another alternative of the immediately preceding embodiment, m is 0 or more, with the proviso that the value of m does not exceed the number of available substitutable hydrogen atoms on ring A; and each $R^A$, when present, is fluoro.

In one such alternative embodiment, m is 0, 1, 2, or 3. In another such alternative embodiment, m is 0, 1, or 2. In another such alternative embodiment, m is 0 or 1.

In one embodiment, in each of Formulas (I), (I'), (IA), and (IA'), ring A is phenyl; and m is 0.

The following alternative embodiments of $R^L$ are contemplated in combination with any of the embodiments described hereinabove.

In one embodiment, in each of Formulas (I), (I'), (IA), and (IA'):

$R^L$ is lower alkyl,
  wherein said lower alkyl of $R^L$ are each optionally unsubstituted or substituted with one or more florine, and
  wherein 1 to 2 non-adjacent, non-terminal carbon atoms in said alkyl are optionally independently replaced with —O—, —NH—, —N(alkyl)-, —S—, —S(O)—, or —S(O)$_2$—.

In one embodiment, in each of Formulas (I), (I'), (IA), and (IA'):

$R^L$ is selected from the group consisting of methyl, ethyl, —CF$_3$, —CHF$_2$, —CH$_2$F, —CH$_2$CF$_3$, —CF$_2$CH$_3$, —CH$_2$OCH$_3$, —CH$_2$OCH$_2$CH$_3$, —CH$_2$CH$_2$OCH$_3$, —CH(OCH$_3$)CH$_3$, —CH$_2$SCH$_3$, —CH$_2$N(CH$_3$)$_2$, —CH$_2$OCF$_3$, and —CH$_2$OCHF$_2$.

In one embodiment, in each of Formulas (I), (I'), (IA), and (IA'):

$R^L$ is selected from the group consisting of methyl, —CHF$_2$, —CH$_2$OCH$_3$, —CH$_2$OCF$_3$, and —CH$_2$OCHF$_2$.

In an alternative of the preceeding embodiments in which $R^L$ is lower alkyl, $L^1$ is a divalent moiety selected from the group consisting of —C(O)NH— and —CH$_2$NH—.

In one embodiment, in each of Formulas (I), (I'), (IA), and (IA'):

-L$_1$- is a divalent moiety selected from the group consisting of —C(O)NH—, —CH$_2$C(O)NH—, —NH—, —CH(CH$_3$)NH— and —CH$_2$NH—; and $R^L$ is a moiety having the formula

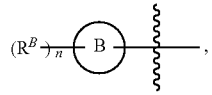

wherein:

ring B is selected from the group consisting of azetidinyl, benzimidazolyl, benzoisothiazolyl, benzoisoxazolyl, benzothiazolyl, benzoxazolyl, cyclobutyl, cyclohexyl, cyclopentyl, cyclopropyl, dihydroindenyl, dihydrooxazolyl, furanyl, imidazolyl, imidazopyridinyl, imidazopyrimidinyl, imidazothiazolyl, indenyl, indolyl, isothiazolyl, isoxazolyl, morpholinyl, oxadiazolyl, oxazolyl, oxetanyl, phenyl, piperazinyl, piperidinyl, pyrazinyl, pyrazolyl, pyrazolopyridinyl, pyrazolopyrimidinyl, pyridazinyl, pyridinyl, pyrimidinyl, pyrrolidinyl, pyrrolyl, pyrrolopyridinyl, pyrrolopyrimidinyl, tetrahydrofuranyl, tetrahydropyranyl, tetrazolyl, thiadiazolyl, thiazolyl, thienyl, thienylpyridine, thiomorpholinyl, thiomorpholinyl dioxide, triazolyl, quinolinyl, isoquinolinyl, naphthyridinyl, phthalazinyl, quinazolinyl, quinoxalinyl, pteridinyl, pyrazinopyridazinyl pyrazinopyridazinyl, pyridopyrazinyl, pyridopyridazinyl, and pyridopyrimidinyl.

In one embodiment, in each of Formulas (I), (I'), (IA), and (IA'):

$L^1$ is —C(O)NH—; and
$R^L$ is a moiety having the formula

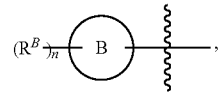

wherein:

ring B is selected from the group consisting of cyclobutyl, cyclopropyl, furanyl, indolyl, isothiazolyl, isoxazolyl, oxadiazolyl, oxazolyl, oxetanyl, phenyl, pyrazinyl, pyrazolyl, pyridazinyl, pyridyl, pyrimidinyl, pyrrolyl, tetrahydrofuranyl, tetrahydropyranyl, thiadiazolyl, thiazolyl, and thienyl.

In an alternative of the immediately preceding embodiment, n is 0 or more, with the proviso that the value of n does not exceed the number of available substitutable hydrogen atoms on ring B; and each $R^B$ group, when present, is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridyl, oxadiazolyl, isoxazolyl, oxazolyl, and pyrrolyl, wherein each said phenyl, pyridyl, oxadiazolyl, isoxazolyl, oxazolyl, and pyrrolyl is optionally substituted with from 1 to 3 substituents independently selected from the group consisting of F, Cl, —CN, —CH$_3$, —OCH$_3$, and —CF$_3$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, n is 0 or more, with the proviso that the value of n does not exceed the number of available substitutable hydrogen atoms on ring B; and each $R^B$ group, when present, is independently selected from the group consisting of fluoro, chloro, bromo, —CN, —OCH$_3$, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —C≡CH, —C≡C—CH$_3$, —CF$_3$, —CHF$_2$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, bromo, —CN, methyl, —OMe, —OCH$_2$—C≡C—H, —CF$_3$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In one embodiment, in each of Formulas (I), (I'), (IA), and (IA'):
L$^1$ is —C(O)NH—; and
R$^L$ is a moiety having the formula

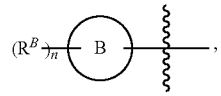

wherein:
ring B is selected from the group consisting of indolyl, isothiazolyl, isoxazolyl, oxadiazolyl, oxazolyl, phenyl, pyrazinyl, pyrazolyl, pyridazinyl, pyridyl, pyrimidinyl, pyrrolyl, thiadiazolyl, thiazolyl, and thienyl.

In an alternative of the immediately preceding embodiment, n is 0 or more, with the proviso that the value of n does not exceed the number of available substitutable hydrogen atoms on ring B; and
each $R^B$ group, when present, is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridyl, oxadiazolyl, isoxazolyl, oxazolyl, and pyrrolyl,
wherein each said phenyl, pyridyl, oxadiazolyl, isoxazolyl, oxazolyl, and pyrrolyl is optionally substituted with from 1 to 3 substituents independently selected from the group consisting of F, Cl, —CN, —CH$_3$, —OCH$_3$, and —CF$_3$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, bromo, —CN, —OCH$_3$, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —C≡CH, —C≡C—CH$_3$, —CF$_3$, —CHF$_2$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, bromo, —CN, methyl, —OMe, —OCH$_2$—C≡C—H, —CF$_3$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In one embodiment, in each of Formulas (I), (I'), (IA), and (IA'):
L$^1$ is —C(O)NH—; and
R$^L$ is a moiety having the formula

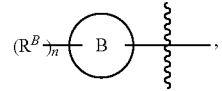

wherein:
ring B is selected from the group consisting of oxazolyl, pyridinyl, and pyrazinyl.

In an alternative of the immediately preceding embodiment, n is 0 or more, with the proviso that the value of n does not exceed the number of available substitutable hydrogen atoms on ring B; and
each $R^B$ group, when present, is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridyl, oxadiazolyl, isoxazolyl, oxazolyl, and pyrrolyl,
wherein each said phenyl, pyridyl, oxadiazolyl, isoxazolyl, oxazolyl, and pyrrolyl is optionally substituted with from 1 to 3 substituents independently selected from the group consisting of F, Cl, —CN, —CH$_3$, —OCH$_3$, and —CF$_3$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, bromo, —CN, —OCH$_3$, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —C≡CH, —C≡C—CH$_3$, —CF$_3$, —CHF$_2$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, bromo, —CN, methyl, —OMe, —OCH$_2$—C≡C—H, —CF$_3$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In one embodiment, in each of Formulas (I), (I'), (IA), and (IA'):
L$_1$ is —NH—; and
R$^L$ is a moiety having the formula

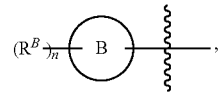

wherein:
ring B is selected from the group consisting of cyclopentyl, cyclohexyl, imidazopyridinyl, imidazopyrimidinyl, morpholino, phenyl, piperidinyl, pyrazinyl, pyrazolyl, pyridazinyl, pyridinyl, pyrimidinyl, pyrrolidinyl, tetrahydrofuranyl, tetrahydropyranyl, naphthyridinyl, pteridinyl, pyrazinopyridazinyl pyridopyrazinyl, pyridopyridazinyl, and pyridopyrimidinyl.

In an alternative of the immediately preceding embodiment, n is 0 or more, with the proviso that the value of n does not exceed the number of available substitutable hydrogen atoms on ring B; and each $R^B$ group, when present, is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridyl, oxadiazolyl, isoxazolyl, oxazolyl, and pyrrolyl, wherein each said phenyl, pyridyl, oxadiazolyl, isoxazolyl, oxazolyl, and pyrrolyl is optionally substituted with from 1 to 3 substituents independently selected from the group consisting of F, Cl, —CN, —CH$_3$, —OCH$_3$, and —CF$_3$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —C≡CH, —C≡C—CH$_3$, —CF$_3$, —CHF$_2$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, —CN, methyl, —OMe, —OCH$_2$—C≡C—H, —CF$_3$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In one embodiment, in each of Formulas (I), (I'), (IA), and (IA'):
$L_1$ is —NH—; and
$R^L$ is a moiety having the formula

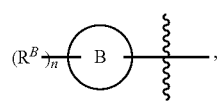

wherein:
ring B is selected from the group consisting of cyclopentyl, phenyl, pyridinyl, pyrimidinyl, naphthyridinyl, pyridopyrimidinyl, pyridopyrazinyl, and pteridinyl.

In an alternative of the immediately preceding embodiment, n is 0 or more, with the proviso that the value of n does not exceed the number of available substitutable hydrogen atoms on ring B; and each $R^B$ group, when present, is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridyl, oxadiazolyl, isoxazolyl, oxazolyl, and pyrrolyl, wherein each said phenyl, pyridyl, oxadiazolyl, isoxazolyl, oxazolyl, and pyrrolyl is optionally substituted with from 1 to 3 substituents independently selected from the group consisting of F, Cl, —CN, —CH$_3$, —OCH$_3$, and —CF$_3$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —C≡CH, —C≡C—CH$_3$, —CF$_3$, —CHF$_2$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, —CN, methyl, —OMe, —OCH$_2$—C≡C—H, —CF$_3$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In one embodiment, in each of Formulas (I), (I'), (IA), and (IA'):
$L_1$ is —NH—; and
$R^L$ is a moiety having the formula

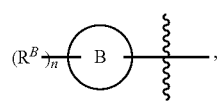

wherein:
ring B is selected from the group consisting of cyclopentyl, naphthyridinyl, and pyridopyrazinyl.

In an alternative of the immediately preceding embodiment, n is 0 or more, with the proviso that the value of n does not exceed the number of available substitutable hydrogen atoms on ring B; and each $R^B$ group, when present, is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridyl, oxadiazolyl, isoxazolyl, oxazolyl, and pyrrolyl, wherein each said phenyl, pyridyl, oxadiazolyl, isoxazolyl, oxazolyl, and pyrrolyl is optionally substituted with from 1 to 3 substituents independently selected from the group consisting of F, Cl, —CN, —CH$_3$, —OCH$_3$, and —CF$_3$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —C≡CH, —C≡C—CH$_3$, —CF$_3$, —CHF$_2$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, —CN, methyl, —OMe, —OCH$_2$—C≡C—H, —CF$_3$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In one embodiment, in each of Formulas (I), (I'), (IA), and (IA'):
$L^1$ is —CH$_2$NH—; and
$R^L$ is a moiety having the formula

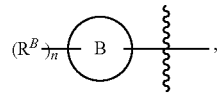

wherein:
ring B is selected from the group consisting of cyclobutyl, cyclohexyl, cyclopentyl, cyclopropyl, furanyl, isothiazolyl, isoxazolyl, oxadiazolyl, oxazolyl, oxetanyl, phenyl, pyrazinyl, pyrazolyl, pyridazinyl, pyridyl, pyrimidinyl, pyrrolyl, tetrahydrofuranyl, tetrahydropyranyl, thiadiazolyl, thiazolyl, and thienyl.

In an alternative of the immediately preceding embodiment, n is 0 or more, with the proviso that the value of n does not exceed the number of available substitutable hydrogen atoms on ring B; and each $R^B$ group, when present, is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridyl, oxadiazolyl, isoxazolyl, oxazolyl, and pyrrolyl,
wherein each said phenyl, pyridyl, oxadiazolyl, isoxazolyl, oxazolyl, and pyrrolyl is optionally substituted with from 1 to 3 substituents independently selected from the group consisting of F, Cl, —CN, —CH$_3$, —OCH$_3$, and —CF$_3$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, n is 0 or more, with the proviso that the value of n does not exceed the number of available substitutable hydrogen atoms on ring B; and
each $R^B$ group, when present, is independently selected from the group consisting of fluoro, chloro, bromo, —CN, —OCH$_3$, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —C≡CH, —C≡C—CH$_3$, —CF$_3$, —CHF$_2$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, bromo, —CN, methyl, —OMe, —OCH$_2$—C≡C—H, —CF$_3$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In one embodiment, in each of Formulas (I), (I'), (IA), and (IA'):
$L^1$ is —CH$_2$NH—; and
$R^L$ is a moiety having the formula

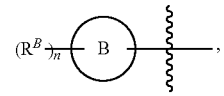

wherein:
ring B is selected from the group consisting of cyclobutyl, cyclopropyl, phenyl, pyrazinyl, pyridyl, pyrimidinyl, tetrahydrofuranyl, and tetrahydropyranyl.

In an alternative of the immediately preceding embodiment, n is 0 or more, with the proviso that the value of n does not exceed the number of available substitutable hydrogen atoms on ring B; and each $R^B$ group, when present, is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridyl, oxadiazolyl, isoxazolyl, oxazolyl, and pyrrolyl,
wherein each said phenyl, pyridyl, oxadiazolyl, isoxazolyl, oxazolyl, and pyrrolyl is optionally substituted with from 1 to 3 substituents independently selected from the group consisting of F, Cl, —CN, —CH$_3$, —OCH$_3$, and —CF$_3$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, bromo, —CN, —OCH$_3$, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —C≡CH, —C≡C—CH$_3$, —CF$_3$, —CHF$_2$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each $R^B$ group, when present, is independently selected from the group consisting of fluoro, chloro, bromo, —CN, methyl, —OMe, —OCH$_2$—C≡C—H, —CF$_3$, —OCF$_3$, and —OCHF$_2$.

In one such alternative embodiment, n is 0, 1, 2, or 3. In another such alternative embodiment, n is 0, 1, or 2. In another such alternative embodiment, n is 0 or 1.

In one embodiment, in each of Formulas (I), (I'), (IA), and (IA'):

L¹ is —CH₂NH—; and

R$^L$ is a moiety having the formula

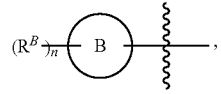

wherein:

ring B is selected from the group consisting of cyclobutyl, cyclopropyl, phenyl, pyrazinyl, and pyridyl.

In an alternative of the immediately preceding embodiment, n is 0 or more, with the proviso that the value of n does not exceed the number of available substitutable hydrogen atoms on ring B; and each R$^B$ group, when present, is independently selected from the group consisting of halogen, oxo, —OH, —CN, —OCH₃, —OCH₂CH₃, —O-cyclopropyl, —O—CH₂-cyclopropyl, —OCH₂—C≡C—H, —OCH₂—C≡C—CH₃, methyl, ethyl, propyl, cyclopropyl, —CH₂-cyclopropyl, —CH₂OCH₃, —CH₂OCH₂CH₃, —C≡CH, —C≡C—CH₃, —CF₃, —CHF₂, —CH₂F, —OCF₃, —OCH₂CF₃, —OCHF₂, —OCH₂F, —OCH₂CH₂F, phenyl, pyridyl, oxadiazolyl, isoxazolyl, oxazolyl, and pyrrolyl, wherein each said phenyl, pyridyl, oxadiazolyl, isoxazolyl, oxazolyl, and pyrrolyl is optionally substituted with from 1 to 3 substituents independently selected from the group consisting of F, Cl, —CN, —CH₃, —OCH₃, and —CF₃.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each R$^B$ group, when present, is independently selected from the group consisting of fluoro, chloro, bromo, —CN, —OCH₃, —O—CH₂-cyclopropyl, —OCH₂—C≡C—H, —OCH₂—C≡C—CH₃, methyl, ethyl, propyl, cyclopropyl, —CH₂-cyclopropyl, —CH₂OCH₃, —C≡CH, —C≡C—CH₃, —CF₃, —CHF₂, —OCF₃, and —OCHF₂.

In one such alternative embodiment, n is 0, 1, 2, or 3. In another such alternative embodiment, n is 0, 1, or 2. In another such alternative embodiment, n is 0 or 1.

In another alternative of the immediately preceding embodiment, each R$^B$ group, when present, is independently selected from the group consisting of fluoro, chloro, bromo, —CN, methyl, —OMe, —OCH₂—C≡C—H, —CF₃, —OCF₃, and —OCHF₂.

In one such alternative embodiment, n is 0, 1, 2, or 3. In another such alternative embodiment, n is 0, 1, or 2. In another such alternative embodiment, n is 0 or 1.

In one embodiment, in each of Formulas (I), (I'), (IA), and (IA'):

L¹ is —CH₂NH—; and

R$^L$ is a moiety having the formula

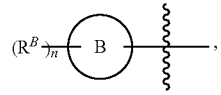

wherein:

ring B is cyclopropyl.

In an alternative of the immediately preceding embodiment, n is 0.

Specific non-limiting examples of compounds of the invention are shown in the table of examples below. While only one tautomeric form of each compound is shown in the tables, it shall be understood that both tautomeric forms of the compounds are contemplated as being within the scope of the non-limiting examples.

In another embodiment, in each of Formulas (I), (I'), (IA), and (IA'), 1 to 3 carbon atoms of the compounds of the invention may be replaced with 1 to 3 silicon atoms so long as all valency requirements are satisfied.

Another embodiment provides a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents which may be useful in combination with the compounds of the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Non-limiting examples of additional therapeutic agents which may be useful in combination with the compounds of the invention include drugs that may be useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from β₂ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Non-limiting examples of additional therapeutic agents for that may be useful in combination with compounds of the invention include: muscarinic antagonists (e.g., m₁ agonists (such as acetylcholine, oxotremorine, carbachol, or McNa343), or m₂ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB 1 receptor inverse agonists or CB 1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention or pharmaceutically acceptable salt thereof, and a pharmaceutically acceptable carrier or diluent.

Another embodiment provides a method of inhibiting β-secretase comprising exposing a population of cells expressing β-secretase to at least one compound of the invention, or a tautomer thereof, in an amount effective to inhibit β-secretase. In one such embodiment, said population of cells is in vivo. In another such embodiment, said population of cells is ex vivo. In another such embodiment, said population of cells is in vitro.

Additional embodiments in which the compounds of the invention may be useful include: a method of inhibiting β-secretase in a patient in need thereof. A method of inhibiting the formation of Aβ from APP in a patient in need thereof. A method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer thereof, or pharmaceutically acceptable salt of said compound or said tautomer, in a therapeutically effective amount to inhibit said pathology or condition in said patient.

Additional embodiments in which the compounds of the invention may be useful include: a method of treating, preventing, and/or delaying the onset of one or more pathologies associated with Aβ and/or one or more symptoms of one or more pathologies associated with Aβ. Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, said method(s) comprising administering to said patient in need thereof at least one compound of the invention, or a tautomer thereof, or pharmaceutically acceptable salt of said compound or said tautomer, in an amount effective to inhibit said pathology or pathologies.

Another embodiment in which the compounds of the invention may be useful includes a method of treating Alzheimer's disease, wherein said method comprises administering an effective (i.e., therapeutically effective) amount of one or more compounds of the invention (or a tautomer thereof, or pharmaceutically acceptable salt of said compound or said tautomer), optionally in further combination with one or more additional therapeutic agents which may be effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

Another embodiment in which the compounds of the invention may be useful includes a method of treating mild cognitive impairment ("MCI"), wherein said method comprises administering an effective (i.e., therapeutically effective) amount of one or more compounds of the invention (or a tautomer thereof, or pharmaceutically acceptable salt of said compound or said tautomer) to a patient in need of treatment. In one such embodiment, treatment is commenced prior to the onset of symptoms.

Another embodiment in which the compounds of the invention may be useful includes a method of preventing, or alternatively of delaying the onset, of mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several years before, an effective (i.e., therapeutically effective), and over a period of time and at a frequency of dose sufficient for the therapeutically effective degree of inhibition of the BACE enzyme over the period of treatment, an amount of one or more compounds of the invention (or a tautomer thereof, or pharmaceutically acceptable salt of said compound or said tautomer) to a patient in need of treatment.

Another embodiment in which the compounds of the invention may be useful includes a method of treating Down's syndrome, comprising administering an effective (i.e., therapeutically effective) amount of one or more compounds of the invention (or a tautomer thereof, or pharmaceutically acceptable salt or solvate of said compound or said tautomer) to a patient in need of treatment.

Another embodiment in which the compounds of the invention may be useful includes a kit comprising, in separate containers, in a single package, pharmaceutical compositions for use in combination, wherein one container comprises an effective amount of a compound of the invention (or a tautomer thereof, or pharmaceutically acceptable salt of said compound or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1 and/or BACE-2.

In various embodiments, the compositions and methods disclosed above and below wherein the compound(s) of the invention is a compound or compounds selected from the group consisting of the exemplary compounds of the invention described herein.

In another embodiment, the invention provides methods of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease. Such methods comprise administering a compound of the invention, or a pharmaceutically acceptable salt thereof, to a patient in need thereof in an amount effective to treat said disease or pathology.

In another embodiment, the invention provides for the use of any of the compounds of the invention for use as a medicament, or in medicine, or in therapy.

In another embodiment, the invention provides for use of a compound of the invention for the manufacture of a medicament for the treatment of a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of"alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine (F), chlorine (Cl), bromine (Br), or iodine (I). Preferred are fluorine, chlorine and bromine.

"Alkyl" means an aliphatic hydrocarbon group, which may be straight or branched, comprising 1 to 10 carbon atoms. "Lower alkyl" means a straight or branched alkyl group comprising 1 to 4 carbon atoms. Branched means that one or more lower alkyl groups such as methyl, ethyl or propyl, are attached to a linear alkyl chain. Non-limiting examples of suitable alkyl groups include methyl (Me), ethyl (Et), n-propyl, isopropyl, n-butyl, i-butyl, and t-butyl.

"Alkenyl" means an aliphatic hydrocarbon group containing at least one carbon-carbon double bond and which may be straight or branched and comprising 2 to 10 carbon atoms in the straight or branched chain. Branched means that one or more lower alkyl groups such as methyl, ethyl propyl, ethenyl or propenyl are attached to a linear or branched alkenyl chain. "Lower alkenyl" means 2 to 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising 2 to 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means 2 to 4 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising 6 to 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

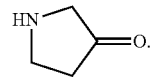

As used herein, the term "monocyclic heterocycloalkyl" refers monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

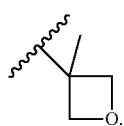

It should be noted that in hetero-atom containing ring systems of this invention, there are no hydroxyl groups on carbon atoms adjacent to a N, O or S, as well as there are no N or S groups on carbon adjacent to another heteroatom.

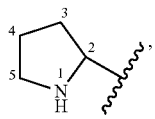

there is no —OH attached directly to carbons marked 2 and 5.

"Alkoxy" means an —O-alkyl group in which the alkyl group is as previously described. Non-limiting examples of alkoxy groups include methoxy, ethoxy, n-propoxy, iso-propoxy and n-butoxy. The bond to the parent moiety is through the oxygen.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^6$ in —$N(R^6)_2$, or a variable appears more than once in a structure presented herein, the variables can be the same or different.

The line _____, as a bond generally indicates a mixture of, or either of, the possible isomers, e.g., containing (R)- and (S)-stereochemistry. For example:

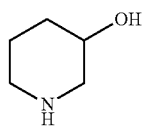

means containing both and

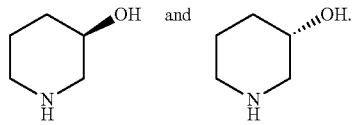

The wavy line ～～, as used herein, indicates a point of attachment to the rest of the compound. Lines drawn into the ring systems, such as, for example:

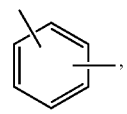

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

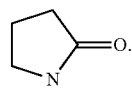

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

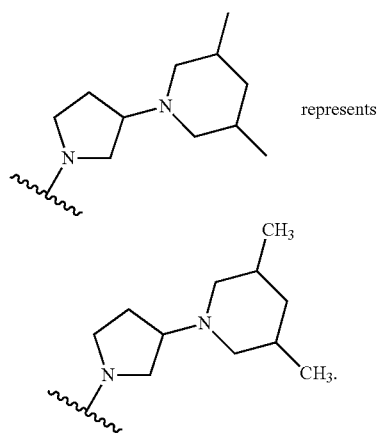

represents

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention. Thus, compounds of the invention conforming to the formula:

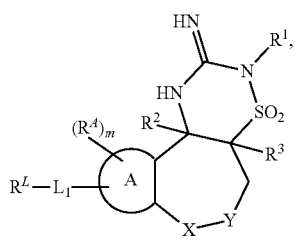

and its tautomer, which can be depicted as:

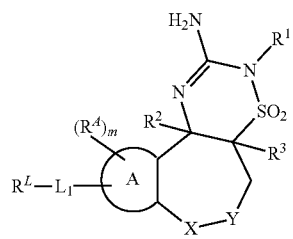

are both contemplated as being within the scope of the compounds of the invention. As noted above, while only one said tautomeric form of each example compound of the invention may be shown in the tables and appended claims, it shall be understood that both tautomeric forms of the compounds are contemplated as being within the scope of the non-limiting example compounds of the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comprising one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for such monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follow:
Acetic acid: AcOH
Acetonitrile: MeCN
Aqueous: aq.
tert-Butyl: t-Bu or tBu
Dichloromethane: DCM
Diisopropylethylamine: DIEA or iPr$_2$NEt
Dimethylformamide: DMF
Dimethylsulfoxide: DMSO
Ethyl: Et
Diethylether: Et$_2$O
Ethanol: EtOH
Ethyl acetate: AcOEt, EtOAc, or EA
Example: Ex.
Grams: g
Hexanes: hex
High performance liquid chromatography: HPLC
Inhibition: Inh.
Liquid chromatography mass Spectrometry: LCMS
Liter: L
Methyl: Me
Methoxyethoxymethyl: MEM
Methanol: MeOH
Microliters: µl or µL
Milligrams: mg
Milliliters: mL
Millimoles: mmol
Minutes: min Molar: M
N-bromosuccinimide: NBS
n-Butyllithium: nBuLi or n-BuLi
N-methylpyrrolidinone: NMP
Nanomolar: nM
Nuclear magnetic resonance spectroscopy: NMR
Number: no. or No.
Observed: Obs.
Para-toluene sulfonate: OTs
Para-methoxy benzyl: PMB
Petroleum ether: PE
Retention time: $t_R$
Room temperature (ambient, about 25° C.): rt or RT
tert-Butoxycarbonyl: t-Boc or Boc
Supercritical Fluid Chromatography: SFC
Temperature: temp.
Titanium (IV) ethoxide: Ti(OEt)$_4$
Triethylamine: Et$_3$N
Trifluoroacetic acid: TFA
Tetrahydrofuran: THF
2,4,6-tripropyl-1,3,5,2,4,6-trioxhosathoriphosphorinane-2,4-6-trioxide: T3P or T$_3$P Method A:

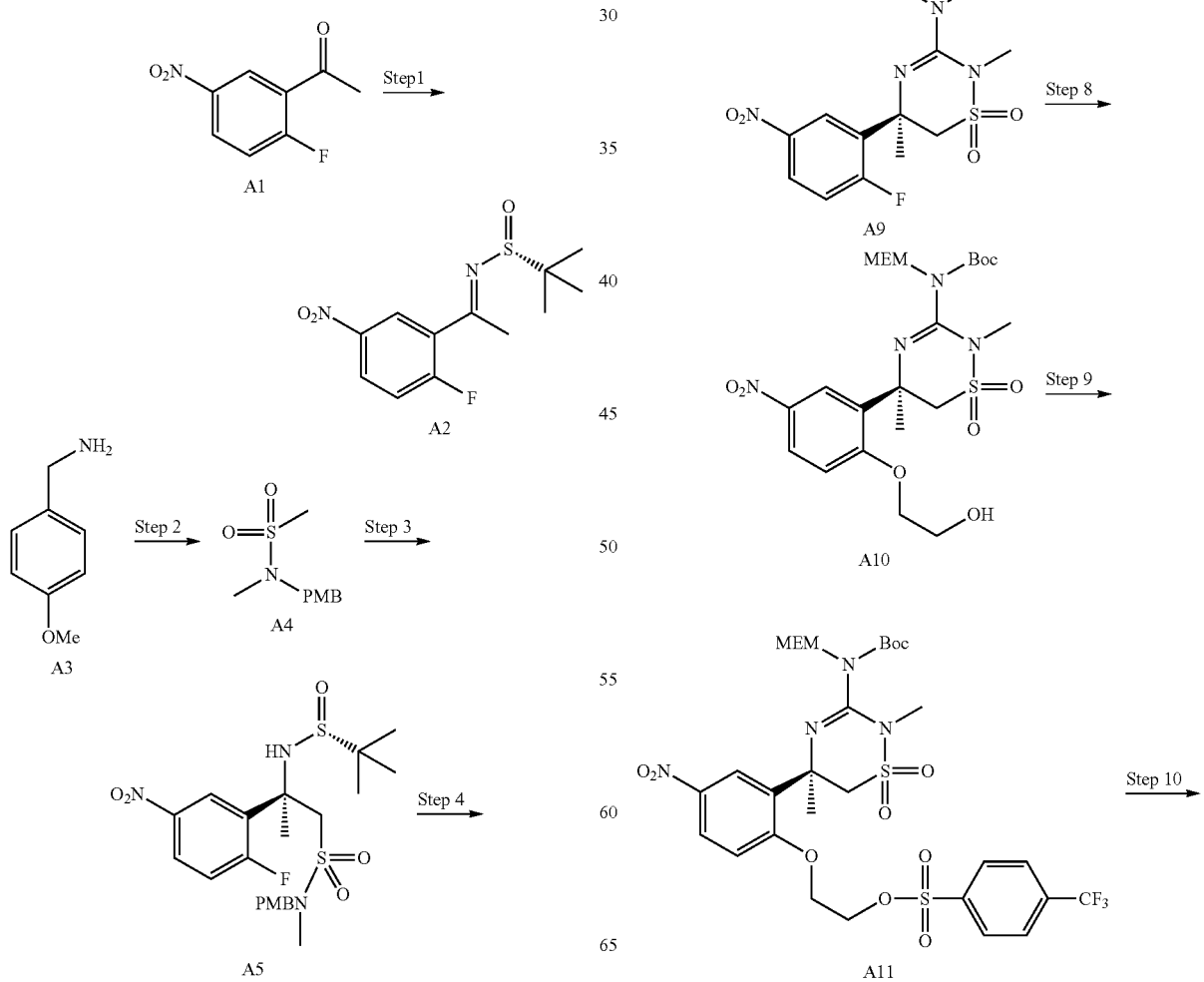

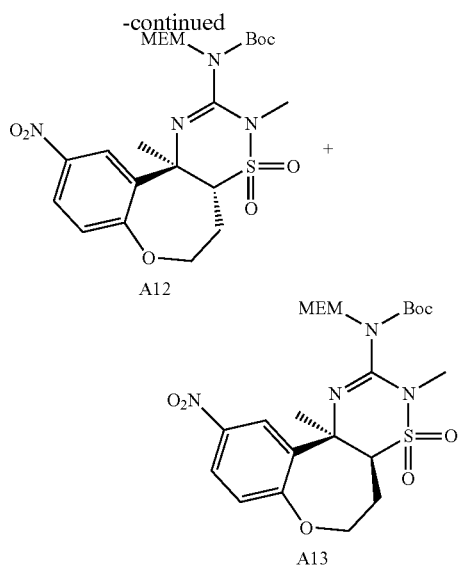

A12

A13

Step 1:

To a solution of acetophenone A1 (115 g, 628 mmol) in anhydrous THF (900 mL) was added (R)-t-butylsulfinimde (83.7 g, 691 mmol) and Ti(OEt)$_4$ (315 g, 1.38 mol). The resultant solution was heated to reflux for 20 hr. The solution was then cooled to RT and poured onto ice (3 kg). The resultant mixture was stirred for 20 min. The mixture was then filtered and the filter cake was washed with CH$_2$Cl$_2$ (3×). The layers were separated and the organic layer was washed with brine, dried over Na$_2$SO$_4$, filtered and concentrated. The crude product was purified via flash chromatography (SiO$_2$; 15% EtOAc/heptane) to afford the ketimine A2.

Step 2:

To a stirred solution of 4-methoxybenzyl amine A3 (199 g, 1.45 mol) in anhydrous pyridine (400 mL) at 0° C. was added dropwise via an addition funnel methanesulfonyl chloride (116 mL, 1.45 mol) over 45 min. After the addition was complete, the cooling bath was removed and the resultant solution was stirred at RT overnight. The reaction was concentrated in vacuo. The slurry was then taken up in DCM (1 L). The organic solution was washed with 1 N HCl (aq.) (2×1 L), sat. NaHCO$_3$ (2×1 L) and brine (1×500 mL). The organic layer was dried over Na$_2$SO$_4$, filtered and concentrated to afford a solid. This solid was dissolved in 95% EtOH (430 mL) with warming. The solution was allowed to cool, and the resulting solid precipitate was removed by filtration. The solid was then washed with cold EtOH (3×150 mL). A second batch of solid was similarly obtained after allowing the mother liquor to stir at RT overnight. The two batches of solid were combined and dissolved in anhydrous DMF (3.0 L), cooled to 0° C. and placed under an atmosphere of N$_2$. To this solution was added in small portions sodium hydride (60% in mineral oil, 60.2 g, 1.51 mol). After the addition was complete, the mixture was stirred for an additional 10 min. To this mixture was added dropwise via an addition funnel methyl iodide (250 g, 1.76 mol). After the addition was complete, the cooling bath was removed and the mixture was allowed to stir at RT overnight. After that time, the mixture was concentrated in vacuo to remove approximately 2.5 L of DMF. The mixture was then partitioned between 5 L ice water, 5 L Et$_2$O and 500 mL of EtOAc. The organic layer was separated. The aqueous layer was extracted with Et$_2$O (2×1 L). The combined organic layers were washed with brine (2×1 L), dried over Na$_2$SO$_4$, filtered and concentrated. The residue was stirred with hexanes, and the resulting solid was removed by filtration and washed with hexanes (2×250 mL). This solid was then dissolved in hexanes/EtOAc (1:1, 450 mL) with warming. The solid formed on cooling was filtered off to afford product A4. The remaining mother liquor was purified via silica gel chromatography (50% EtOAc/hexanes) to afford additional A4.

Step 3:

To a solution of sulfonamide A4 (38.0 g, 166 mmol) in anydrous THF (500 mL) at −78° C. under an atmosphere of N$_2$ was slowly added a solution of n-BuLi (1.6 M in hexanes, 104 mL, 166 mmol). The resultant solution was stirred at −78° C. for 30 min. After that time, a precooled (−78° C.) solution of ketimine A2 (23.7 g, 82.8 mmol) in anhydrous THF (200 mL) was added to the reaction mixture via cannula. The resulting mixture was allowed to stir at −78° C. for 1 hour. After that time, water and EtOAc were added to the reaction. The cooling bath was removed and the mixture was allowed to warm to RT. The aqueous layer was then separated and extracted with EtOAc (3×). The combined organic layers were washed with brine, dried over Na$_2$SO$_4$, filtered and concentrated. The crude product was purified via flash chromatography (SiO$_2$; gradient elution 100:0 to 40:60 hexanes:EtOAc) to afford A5.

Step 4:

To a solution of A5 (27.4 g, 53.1 mmol) in CH$_2$Cl$_2$: MeOH (3:1, 230 mL) was added a solution of HCl (4 M in dioxane, 80 mL, 319 mmol). The resultant solution was stirred at RT for 45 min. The solution was then concentrated. The crude residue was taken up in toluene (100 mL) and concentrated in vacuo (2×). The residue was dissolved in CH$_2$Cl$_2$ (230 mL). To this solution was added TFA (61.4 mL, 797 mmol) and 1,3-dimethoxybenzene (42 mL, 319 mmol). The resultant solution was stirred at RT overnight. The solution was then concentrated to approximately ¼ the original volume. The solution was partitioned between 1 M HCl (aq.) (1 L) and Et$_2$O (500 mL). The aqueous layer was separated and extracted with Et$_2$O (2×500 mL). The organic layers were combined and back-extracted with 1 N HCl (1×250 mL). The aqueous layers were then combined, adjusted to approximately pH 10 with the slow addition of solid Na$_2$CO$_3$, and then extracted with CH$_2$Cl$_2$ (4×300 mL). The organic layers were combined, dried over Na$_2$SO$_4$, filtered and concentrated to afford A6.

Step 5:

To a slurry of amine A6 (13.7 grams, 47 mmol) in n-butanol (150 mL) was added a solution of cyanogen bromide (5 M in MeCN, 10.3 mL, 51 mmol). The resultant mixture was heated to reflux for 4 hours. The mixture was then concentrated to approximately ⅓ of the original volume. To the mixture was added Et$_2$O (200 mL). The resultant solid was removed via filtration and the solid was washed with Et$_2$O (2×). The solid was partitioned between EtOAc and sat. Na$_2$CO$_3$ (aq.). The aqueous layer was extracted with EtOAc (3×). The combined organic layers were washed with brine, dried over Na$_2$SO$_4$, filtered and concentrated to afford A7. This material was carried onto the next step without further purification.

Step 6:

To a solution of A7 (4.0 grams 11.6 mmol) in CH$_2$Cl$_2$ (100 mL) was added Et$_3$N (2.26 mL, 16.2 mmol) and Boc$_2$O (3.3 g, 15.1 mmol). The resultant solution was stirred at RT overnight. After that time, the solution was washed with sat. Na$_2$CO$_3$ (aq.). The Na$_2$CO$_3$ (aq.) was back-extracted with CH$_2$Cl$_2$ (3×). The organic layers were dried over $Na_2SO_4$, filtered and concentrated. The crude product was purified via flash chromatography ($SiO_2$, gradient elution 100:0 to 70:30 hexanes:EtOAc) to afford A8.

Step 7:

To a solution of A8 (64 g, 154 mmol) in DMF (640 ml) at 0° C. was added sodium hydride (18.44 g, 461 mmol). The mixture was stirred at 0° C. for 40 min. To this mixture was added 1-(chloromethoxy)-2-methoxyethane (57.4 g, 461 mmol) and the mixture was stirred at room temperature for 3 h. The reaction mixture was then poured into cold water and the aqueous layer was extracted with EtOAc. The combined organic layers were washed with water and brine then dried over anhydrous $Na_2SO_4$ and concentrated in vacuo. The crude residue was purified by flash chromatography over silica gel (gradient elution 0-40% EtOAc in petroleum ether) to afford A9.

Step 8:

To a solution of ethane-1,2-diol (862 g, 13.9 mol) in NMP (775 ml) was added $K_2CO_3$ (51.0 g, 369 mmol) at RT in portions. The mixture was stirred at 50° C. for 30 min. After that time, A9 (62 g, 123 mmol) was added in portions. The mixture was stirred at 50° C. for 3 h. Afterwhich the reaction mixture was poured into cold water and the aqueous layer was extracted with ethyl acetate. The combined organic layers were washed with water and brine then dried over anhydrous $Na_2SO_4$ and concentrated in vacuo. The crude residue was purified by flash chromatography over silica gel (gradient elution 20-60% EtOAc in petroleum ether) to afford A10.

Step 9:

Into a round-bottom flask purged and maintained with an inert atmosphere of nitrogen, was placed a solution of A10 (43 g, 79 mmol) in DCM (860 ml), the reaction mixture was cooled to 0° C. To the mixture was then added triethylamine (23.88 g, 236 mmol) and DMAP (0.288 g, 2.360 mmol) followed by the portionwise addition of 4-(trifluoromethyl) benzene-1-sulfonyl chloride (25.0 g, 102 mmol). The resultant mixture was stirred for 3 h at 0° C. After that time, the mixture was diluted with 100 mL of $H_2O$. The mixture was then extracted with DCM (3×100 mL). The combined organic layers were washed with brine, dried over anhydrous sodium sulfate, and concentrated in vacuo. The crude residue was purified by flash chromatography over silica gel (gradient elution 9-25% EtOAc in petroleum ether) to afford A11.

Step 10:

To a solution of A11 (48 g, 63.6 mmol) in THF (2400 ml) was added a solution of potassium bis(trimethylsilyl)amide (95 ml, 95 mmol) in portions at 20° C. The mixture was stirred at 20° C. for 15 min. After that time, the reaction mixture was quenched with saturated $NH_4Cl$ solution and extracted with ethyl acetate. The combined organic layers were washed with water and brine, then dried over anhydrous $Na_2SO_4$ and concentrated in vacuo. The crude residue was purified by flash chromatography over silica gel (gradient elution 9-70% EtOAc in petroleum ether) to afford A12 and a residue containing A13 which was further purified by reverse phase flash chromatography (C18 silica gel; gradient elution 40-60% MeCN in $H_2O$) to afford A13.

Method B:

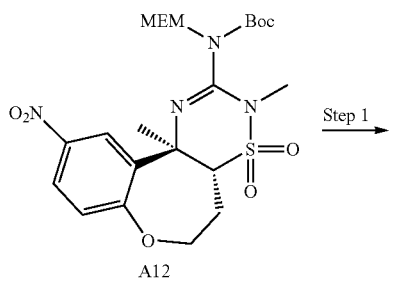

Step 1:

To a solution of A12 (100 mg, 0.189 mmol) in methanol (2 mL) was added zinc (62 mg, 0.946 mmol), ammonium chloride (51 mg, 0.946 mmol). The resulting mixture was stirred at room temperature for 1 h. After that time, the reaction mixture was filtered through celite and the filter cake was washed with a 1:1 mixture of methanol and dichloromethane and concentrated to afford B1 which was carried on without further purification.

41

Step 2:

To a solution of 5-chloropicolinic acid (37.4 mg, 0.240 mmol) in dichloromethane (3 mL) at room temperature (under nitrogen) was added N,N-diisopropylethylamine (0.05 mL, 0.301 mmol) and 50% solution of T₃P in ethyl acetate (0.19 mL, 0.301 mmol). The reaction mixture was stirred at room temperature for 15 min. B1 (100 mg, 0.200 mmol) dissolved in dichloromethane (2 mL) was then added slowly to the reaction mass and the reaction mixture was further stirred at room temperature for 3 h. After the completion of the reaction, the reaction was quenched by adding water, extracted with ethyl acetate and the combined organic layer was washed with water, brine, dried over anhydrous Na₂SO₄ and concentrated to yield the crude product. The crude thus obtained was purified by flash column chromatography over silica gel using 45-50% ethyl acetate in pet ether to afford B2. m/z: 638.4 (M+H)⁺

Step 7:

To a solution of B2 (80 mg, 0.125 mmol) was added trifluoroacetic acid (2 mL) at room temperature and the reaction mixture was heated to reflux for 14 h. The reaction mixture was concentrated under reduced pressure. The residue was partitioned between DCM and 10% NaHCO₃. The organic layer was separated and concentrated in vacuo. The crude thus obtained was purified by flash column chromatography over silica gel using 95-100% ethyl acetate in pet ether to afford Example 1.

42

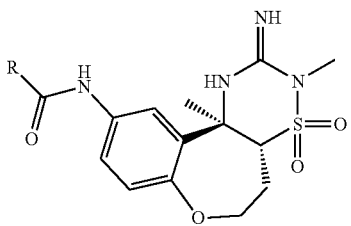

Examples 2-9

Parallel preparation of Examples 2-9: To a set of vials containing the requisite carboxylic acid (0.034 mmol) was added a solution of B1 (17 mg, 0.034 mmol) in DCM (0.75 mL) followed by the addition of iPr₂NEt (0.033 mL, 0.19 mmol) and a solution of T3P (50% in EtOAc, 0.041 mL, 0.068 mmol). The vials were capped and the mixtures were stirred at RT for 48 hours. After that time, water (0.050 mL)

TABLE 1

| Ex | Structure IUPAC Name | LCMS m/z | BACE-1 $K_i$ (nM) | BACE-2 $K_i$ (nM) |
|---|---|---|---|---|
| 1 | 5-chloro-N-((4aR,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)picolinamide | 450.2 | 72 | 65 |

Method C:

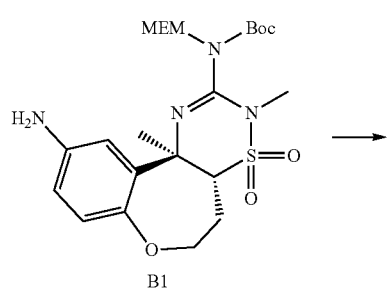

and TFA (0.50 mL) were added to each vial. The mixtures were then heated to 50° C. with stirring overnight. After that time, the mixtures were concentrated in vacuo. The crude residues were dissolved in DMSO (1 mL) and filtered. The crude products were purified by mass triggered SFC using the following conditions: [column: Waters 2-ethylpyridine, 5 μm, 30×150 mm; solvent: gradient range 10% initial to 30-45% final MeOH in CO₂ 100 mL/min; backpressure: 120 bar, 8 min run time] to afford Examples 2-5. The remaining samples were repurified by mass triggered HPLC using the following conditions: [column: Waters XBridge C18, 5 am, 19×100 mm; solvent: gradient range 10-20% initial to 34-50% final MeCN (0.1% NH₄OH) in water (0.1% NH₄OH) 25 mL/min; 9 min run time] to afford Examples 6-9.

TABLE 2

| Ex | Structure / IUPAC Name | LCMS m/z | BACE-1 $K_i$ (nM) | BACE-2 $K_i$ (nM) |
|---|---|---|---|---|
| 2 | N-((4aR,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)picolinamide | 416.13 | 508 | 279 |
| 3 | N-((4aR,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)-2,5-dimethyloxazole-4-carboxamide | 434.14 | 265 | 384 |
| 4 | N-((4aR,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)-2-methoxyacetamide | 383.13 | 1360 | 890 |
| 5 | 5-cyano-N-((4aR,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)picolinamide | 441.13 | 47 | 303 |

TABLE 2-continued

| Ex | Structure / IUPAC Name | LCMS m/z | BACE-1 $K_i$ (nM) | BACE-2 $K_i$ (nM) |
|---|---|---|---|---|
| 6 | N-((4aR,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)-5-(prop-2-yn-1-yloxy)picolinamide | 470.14 | 25 | 995 |
| 7 | 5-fluoro-N-((4aR,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)picolinamide | 434.12 | 108 | 159 |
| 8 | 5-fluoro-N-((4aR,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)-3-methylpicolinamide | 448.14 | 133 | 86 |
| 9 | N-((4aR,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)-5-methoxypyrazine-2-carboxamide | 447.14 | 591 | 5613 |

Method D:

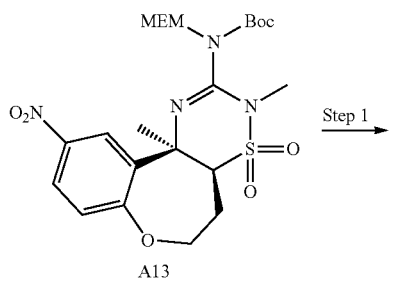

A13

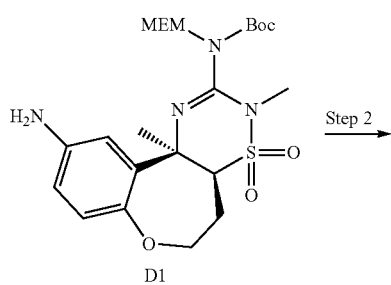

D1

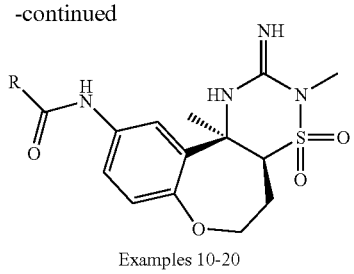

Examples 10-20

Step 1:
To a solution of A13 (200 mg, 0.39 mmol) in a mixture of EtOH (1 mL), THF (4 mL), and water (0.3 mL) was added zinc (247 mg, 3.8 mmol) and ammonium chloride (101 mg, 1.9 mmol). The resulting mixture was heated to 85° C. with stirring for 2 h. After that time, the mixture was cooled to RT, diluted with EtOAc and filtered through celite. The volatiles were then removed in vacuo. The residue was partitioned between EtOAc and brine. The aqueous layer was then extracted with EtOAc (2×). The combined organic layers were dried over $Na_2SO_4$, filtered and concentrated. The crude product was purified via flash chromatography ($SiO_2$ gradient elution 100:0 to 20:80 hexanes:EtOAc) to afford D1.

Step 2:
Parallel preparation of Examples 10-20. These examples were prepared following a procedure similar to that described in Method C. The crude products were purified by mass triggered HPLC using the following conditions: [column: Waters XBridge C18, 5 μm, 19×100 mm; solvent: gradient range 20-35% initial to 55-70% final MeCN (0.1% $NH_4OH$) in water (0.1% $NH_4OH$) 25 mL/min; 8 min run time] to afford Examples 10-20.

| Ex | Structure IUPAC Name | LCMS m/z | BACE-1 $K_i$ (nM) | BACE-2 $K_i$ (nM) |
|---|---|---|---|---|
| 10 | N-((4aS,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)picolinamide | 416.13 | 35 | 15 |
| 11 | N-((4aS,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)-2,5-dimethyloxazole-4-carboxamide | 484.05 | 2 | 2 |

-continued

| Ex | Structure / IUPAC Name | LCMS m/z | BACE-1 $K_i$ (nM) | BACE-2 $K_i$ (nM) |
|---|---|---|---|---|
| 12 | 5-(difluoromethoxy)-N-((4aS,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)picolinamide | 482.12 | 5 | 58 |
| 13 | 5-chloro-3-fluoro-N-((4aS,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)picolinamide | 468.08 | 4 | 4 |
| 14 | 5-fluoro-N-((4aS,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)picolinamide | 434.12 | 10 | 6 |
| 15 | 5-fluoro-N-((4aS,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)-3-methylpicolinamide | 452.11 | 10 | 6 |

-continued

| Ex | Structure / IUPAC Name | LCMS m/z | BACE-1 $K_i$ (nM) | BACE-2 $K_i$ (nM) |
|---|---|---|---|---|
| 16 | 5-cyano-N-((4aS,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)picolinamide | 441.13 | 1 | 14 |
| 17 | N-((4aS,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)-5-methylpicolinamide | 430.15 | 18 | 16 |
| 18 | N-((4aS,11bR)-2-imino-3,11b-dimethyl-4,4-thoxido-2,3,4a,5,6,11b-hexahydro-1H-benzo[2,3]oxepino[4,5-e][1,2,4]thiadiazin-10-yl)-5-(trifluoromethyl)picolinamide | 484.12 | 11 | 79 |
| 19 | N-((4aS,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)-5-(trifluoromethoxy)picolinamide | 500.11 | 8 | 104 |

| Ex | Structure IUPAC Name | LCMS m/z | BACE-1 $K_i$ (nM) | BACE-2 $K_i$ (nM) |
|---|---|---|---|---|
| 20 | 3-chloro-N-((4aS,11bR)-2-imino-3,11b-dimethyl-4,4-dioxido-2,3,4a,5,6,11b-hexahydro-1H-benzo[2,3]oxepino[4,5-e][1,2,4]thiadiazin-10-yl)-5-(trifluoromethyl)picolinamide | 518.08 | 5 | 36 |
Method E:
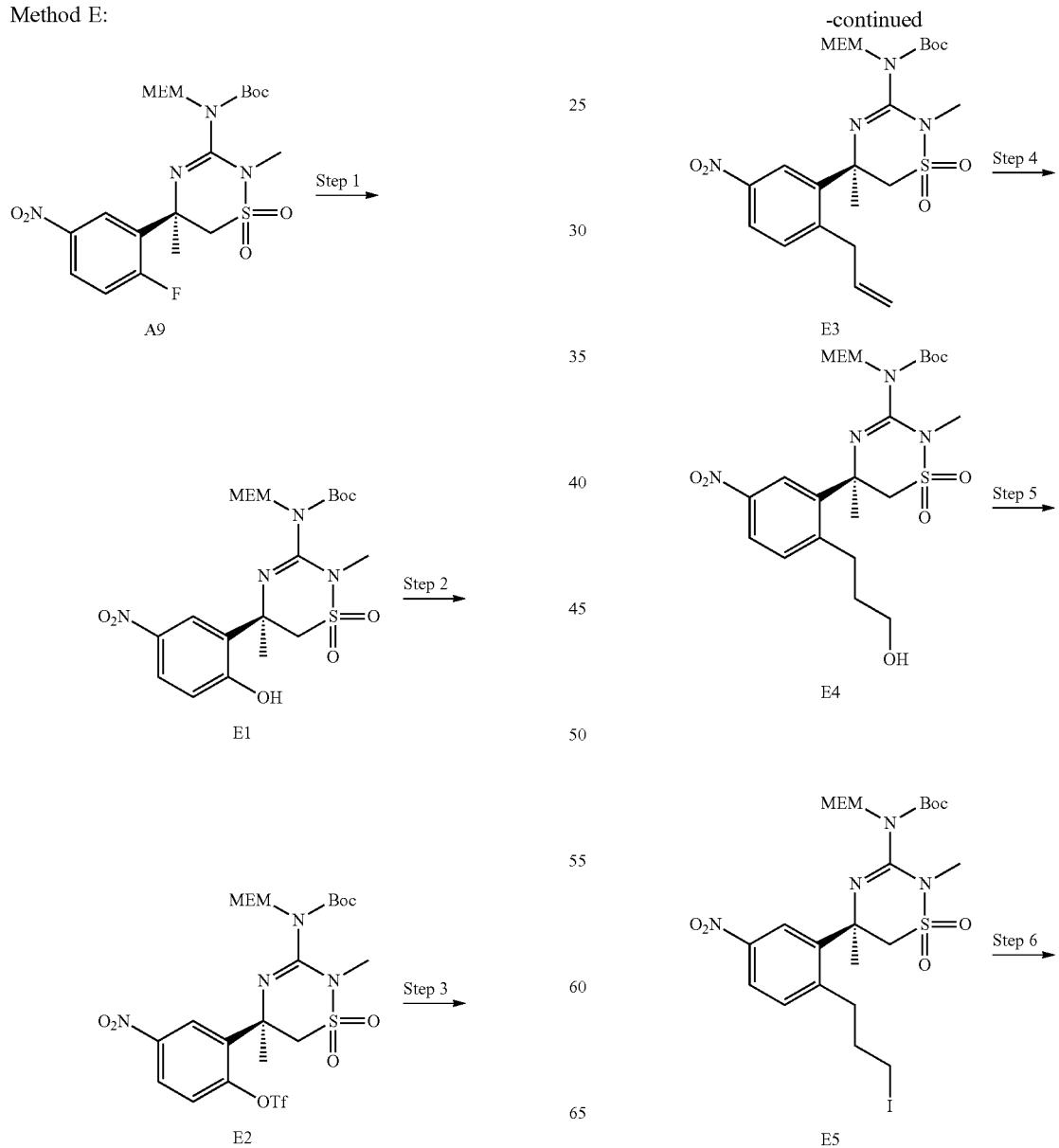

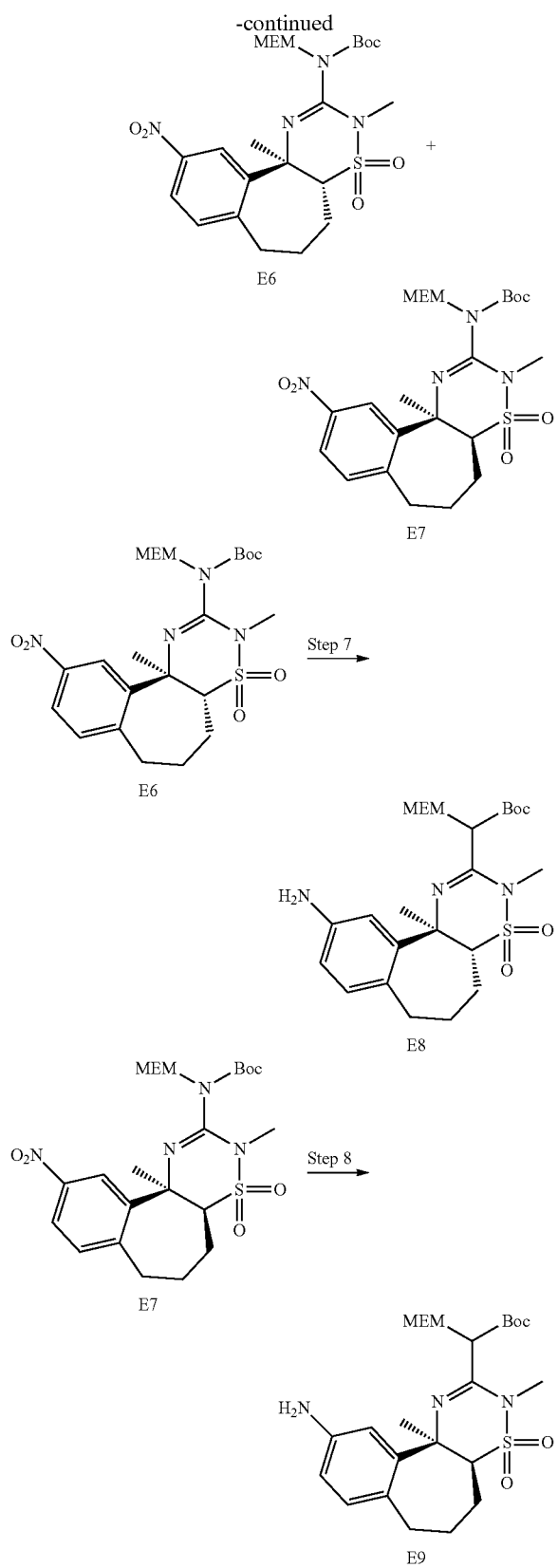

and Cs$_2$CO$_3$ (181 g, 555 mmol) and the mixture was stirred overnight at r.t. After that time, additional Cs$_2$CO$_3$ (90 g, 1.0 eq) and 2-(methylsulfonyl)ethanol (34 g, 1.0 eq) were added and stirring continued for an additional 8 hrs. Additional Cs$_2$CO$_3$ (90 g, 1.0 eq) and 2-(methylsulfonyl)ethanol (34 g, 1.0 eq) were added and stirring continued for additional 16 hrs. The mixture was then diluted with EA and H$_2$O. The organic layer was separated and washed sequentially with water (2×) and brine followed by concentration to afford E1 that was carried on without further purification.

Step 2:

Into a 5000-mL 3-necked round-bottom flask, was placed a solution of E1 (135 g, 201 mmol) in CH$_2$Cl$_2$ (2700 ml) followed by the addition of DIPEA (78 g, 604 mmol). The reaction mixture was cooled to −78° C. To the mixture was then added trifluoromethanesulfonic anhydride (85 g, 302 mmol) dropwise with stirring at −78° C. The resulting mixture was stirred for 1 h at −70° C. in a liquid nitrogen bath. The reaction was then quenched by the addition of 500 mL of NaHCO$_3$ (aq). The resulting mixture was extracted with of CH$_2$Cl$_2$ (3×1000 mL), the combined organic layers were dried over anhydrous sodium sulfate followed by concentration in vacuo. The residue was purified by silica gel chromatography eluting with a gradient of ethyl acetate in petroleum ether (0-20%) to afford E2.

Step 3:

Into a 40-mL sealed tube, was placed a solution of E2 (3.0 g, 4.73 mmol) in toluene (24 mL). This was followed by the addition of potassium acetate (1.40 g, 14 mmol), nitrogen was then passed through the mixture for 3 mins followed by the addition of allyltributylstannane (3.13 g, 9.45 mmol). Nitrogen was then passed through the mixture for 3 mins followed by the addition of lithium chloride (0.601 g, 14.18 mmol). Nitrogen was then passed through the mixture for 3 mins. To the mixture was then added Pd(PPh$_3$)$_4$ (0.546 g, 0.473 mmol). The resulting mixture was stirred for 1 h at 100° C. After that time, the reaction mixture was cooled to RT. The solids were filtered out and the filter cake was washed with toluene (4×30 mL). The combined filtrates were concentrated in vacuo. The residue was purified by silica gel chromatography eluting with a gradient of ethyl acetate in petroleum ether (0-30%) to afford E3.

Step 4:

A solution of E3 (13 g, 24 mmol) in THF (260 ml) and was added a solution of borane-THF complex (1M, 27.2 ml, 27.2 mmol) dropwise at RT. The mixture was stirred for 0.5 h at RT, then the mixture was cooled to 0° C. and treated with water (27 mL), hydrogen peroxide (28.0 g, 247 mmol) and a solution of sodium hydroxide (2N, 24.69 ml, 49.4 mmol). The resultant mixture was stirred at RT for 40 min. After that time, the mixture was partitioned between EA (500 mL) and water (100 mL). The organic layer was separated and washed with brine then concentrated. The residue was purified by silica gel chromatography eluting with a gradient of ethyl acetate in petroleum ether (0-50%) to afford E4.

Step 5:

A solution of imidazole (8.62 g, 127 mmol) and triphenylphosphine (13.29 g, 50.7 mmol) in CH$_2$Cl$_2$ (230 ml) was cooled to 0° C. Iodine (12.86 g, 50.7 mmol) was then added to the reaction mixture and the mixture was stirred for 5 min at 0° C. After that time, a solution of E4 (23 g, 42.2 mmol) in CH$_2$Cl$_2$ (230 ml) was added. The mixture was stirred at RT for 30 min and then concentrated. The residue was purified by silica gel chromatography eluting with a gradient of ethyl acetate in petroleum ether (0-40%) to afford E5.

Step 1:

To a solution of A9 (140 g, 277 mmol) in DMF (1400 ml) was added 2-(methylsulfonyl)ethanol (68.9 g, 555 mmol)

Step 6:

Into a 2000-mL 3-necked round-bottom flask purged and maintained under an inert atmosphere of nitrogen, was placed a solution of E5 (23.5 g, 35.9 mmol) in THF (1200 mL). The mixture was then cooled to −78° C. followed by the addition of a solution of lithium bis(trimethylsilyl)amide (1M, 64.6 ml, 64.6 mmol) dropwise. The mixture was stirred at −70° C. for 40 min. The reaction mixture was then quenched with a saturated NH$_4$Cl solution and the resultant mixture was extracted with ethyl acetate. The combined organic layers were washed with water and brine then dried over anhydrous Na$_2$SO$_4$ and concentrated in vacuo. The residue was purified by silica gel chromatography eluting with a gradient of DCM in petroleum ether (0-30%) followed by EtOAc in petroleum ether (0-30%) to afford E6 and E7. E6: (ES, m/z): 527 [M+H]$^+$; E7: (ES, m/z): 527 [M+H]$^+$.

Step 7:

E8 was prepared from E6 using the procedure described in Method B, Step 1. (ES, m/z): 497.96 [M+H]$^+$ Step 8:

E9 was prepared from E7 using the procedure described in Method B, Step 1. (ES, m/z): 497.31 [M+H]$^+$ Method F:

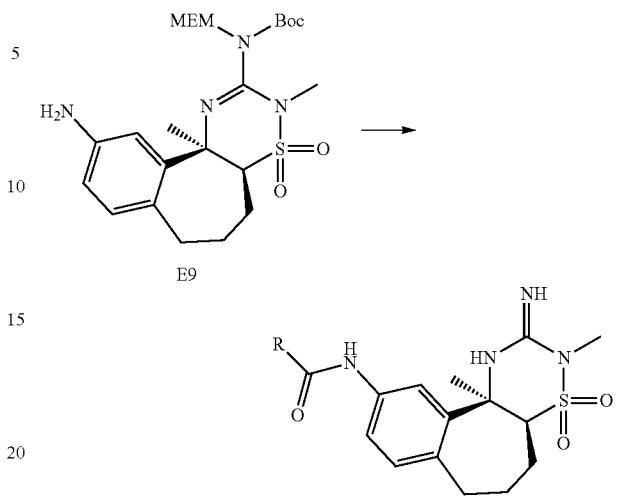

Examples 21-36 were prepared from E9 and the requisite carboxylic acids following the procedure described in Method D.

| Ex | Structure<br>IUPAC Name | LCMS m/z | BACE-1 K$_i$ (nM) | BACE-2 K$_i$ (nM) |
|---|---|---|---|---|
| 21 | N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)-5-methylpicolinamide | 428.19 | 45 | 34 |
| 22 | 5-(difluoromethoxy)-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)picolinamide | 480.11 | 10 | 90 |

| Ex | Structure IUPAC Name | LCMS m/z | BACE-1 $K_i$ (nM) | BACE-2 $K_i$ (nM) |
|---|---|---|---|---|
| 23 | 5-chloro-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)picolinamide | 448.08 | 7 | 7 |
| 24 | N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)-5-methylpyrazine-2-carboxamide | 429.13 | 168 | 251 |
| 25 | 5-chloro-3-fluoro-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)picolinamide | 466.08 | 7 | 5 |
| 26 | 3,5-difluoro-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)picolinamide | 450.16 | 18 | 10 |

| Ex | Structure IUPAC Name | LCMS m/z | BACE-1 $K_i$ (nM) | BACE-2 $K_i$ (nM) |
|---|---|---|---|---|
| 27 | 5-bromo-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)-3-methoxypicolinamide | 524.04 | 18 | 10 |
| 28 | 5-fluoro-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)picolinamide | 432.15 | 18 | 7 |
| 29 | N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)-5-(trifluoromethoxy)picolinamide | 498.13 | 14 | 144 |
| 30 | 3-chloro-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)-5-(trifluoromethyl)picolinamide | 516.08 | 10 | 82 |

| Ex | Structure IUPAC Name | LCMS m/z | BACE-1 $K_i$ (nM) | BACE-2 $K_i$ (nM) |
|---|---|---|---|---|
| 31 | 5-fluoro-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)-3-methylpicolinamide | 446.11 | 19 | 10 |
| 32 | N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)-5-methoxy-3-methylpicolinamide | 458.20 | 27 | 34 |
| 33 | 5-fluoro-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)-3-methylpicolinamide | 459.16 | 48 | 86 |
| 34 | 5-fluoro-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)-3-methylpicolinamide | 445.12 | 17 | 52 |

-continued

| Ex | Structure IUPAC Name | LCMS m/z | BACE-1 $K_i$ (nM) | BACE-2 $K_i$ (nM) |
|---|---|---|---|---|
| 35 | 5-cyano-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)-3-methylpicolinamide | 453.19 | 19 | 10 |
| 36 | 5-cyano-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)picolinamide | 439.09 | 4 | 25 |

Method G:

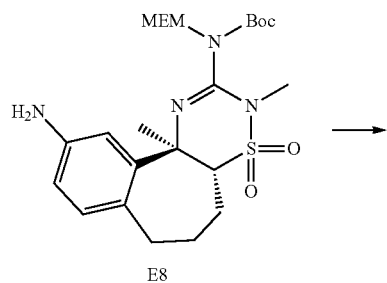

E8

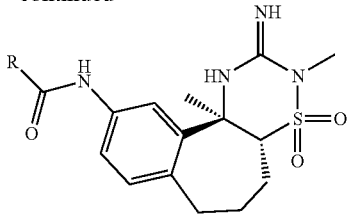

Examples 37-40

Examples 37-40 were prepared from E8 and the requisite carboxylic acids following the procedure described in Method D.

| Ex | Structure IUPAC Name | LCMS m/z | BACE-1 $K_i$ (nM) | BACE-2 $K_i$ (nM) |
|---|---|---|---|---|
| 37 | 5-fluoro-N-((4aR,11bR)-2-imino-3,11b-dimethyl-4,4-dioxido-1,2,3,4a,5,6,7,11b-octahydrobenzo[6,7]cyclohepta[1,2-e][1,2,4]thiadiazin-10- | 432.14 | 159 | 96 |

-continued

| Ex | Structure IUPAC Name | LCMS m/z | BACE-1 $K_i$ (nM) | BACE-2 $K_i$ (nM) |
|---|---|---|---|---|
| | yl)picolinamide | | | |
| 38 | 5-(difluoromethoxy)-N-((4aR,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)picolinamide | 480.11 | 80 | 857 |
| 39 | 5-chloro-N-((4aS,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)picolinamide | 439.13 | 60 | 315 |
| 40 | N-((4aR,11bR)-2-imino-3,11b-dimethyl-4,4-dioxido-1,2,3,4a,5,6,7,11b-octahydrobenzo[6,7]cyclohepta[1,2-e][1,2,4]thiadiazin-10-yl)-5-methylpyrazine-2-carboxamide | 429.17 | 1386 | 2714 |

Method H:

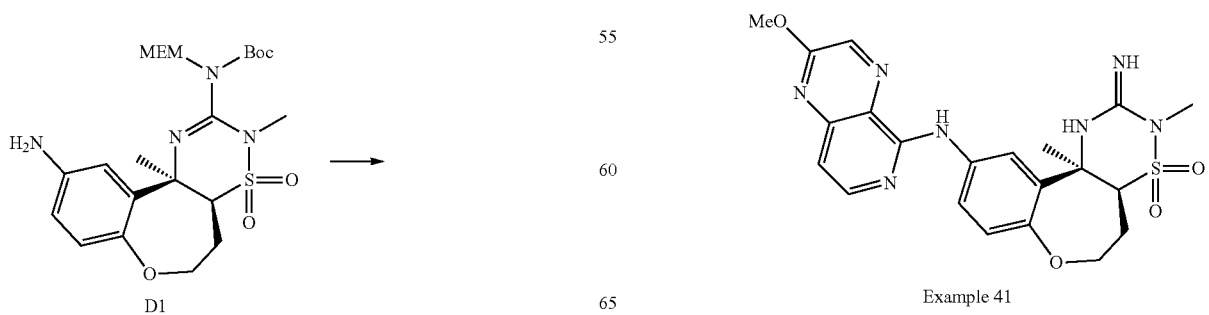

Example 41

A mixture of D1 (20 mg, 0.040 mmol), 5-chloro-2-methoxypyrido[3,4-b]pyrazine (8.24 mg, 0.042 mmol) and HCl/Dioxane (20 μL) in t-BuOH (1 ml) was stirred at 100° C. for 1 h. The mixture was purified by preparative HPLC (with TFA as an additive) to afford Example 41. Following procedures similar to Method H, Examples 42-46 were prepared.

| Ex | Structure / IUPAC Name | LCMS m/z | BACE-1 K$_i$ (nM) | BACE-2 K$_i$ (nM) |
|---|---|---|---|---|
| 41 | (4aS,11bR)-2-imino-10-((2-methoxypyrido[3,4-b]pyrazin-5-yl)amino)-3,11b-dimethyl-2,3,4a,5,6,11b-hexahydro-1H-benzo[2,3]oxepino[4,5-e][1,2,4]-thiadiazine 4,4-dioxide | 470.1 | 60 | 135 |
| 42 | (4aS,11bR)-2-imino-10-((7-methoxy-1,5-naphthyridin-4-yl)amino)-3,11b-dimethyl-2,3,4a,5,6,11b-hexahydro-1H-benzo[2,3]oxepino[4,5-e][1,2,4]-thiadiazine 4,4-dioxide | 469.1 | 412 | 1787 |
| 43 | (4aS,11bR)-2-imino-10-((3-methoxy-1,7-naphthyridin-8-yl)amino)-3,11b-dimethyl-2,3,4a,5,6,11b-hexahydro-1H-benzo[2,3]oxepino[4,5-e][1,2,4]-thiadiazine 4,4-dioxide | 469.1 | 57 | 148 |
| 44 | (4aS,11bR)-2-imino-10-((2-methoxypyrido[3,4-b]pyrazin-5-yl)amino)-3,11b-dimethyl-1,2,3,4a,5,6,7,11b-octahydrobenzo[6,7]cyclohepta[1,2-e][1,2,4]-thiadiazine 4,4-dioxide | 468.1 | 45 | 173 |

| Ex | Structure IUPAC Name | LCMS m/z | BACE-1 $K_i$ (nM) | BACE-2 $K_i$ (nM) |
|---|---|---|---|---|
| 45 | (4aS,11bR)-2-imino-10-((3-methoxypyrido[2,3-b]pyrazin-8-yl)amino)-3,11b-dimethyl-1,2,3,4a,5,6,7,11b-octahydrobenzo[6,7]cyclohepta[1,2-e][1,2,4]-thiadiazine 4,4-dioxide | 468.1 | 547 | 2439 |
| 46 | (4aS,11bR)-2-imino-10-((3-methoxy-1,7-naphthyridin-8-yl)amino)-3,11b-dimethyl-1,2,3,4a,5,6,7,11b-octahydrobenzo[6,7]cyclohepta[1,2-e][1,2,4]-thiadiazine 4,4-dioxide | 467.2 | 108 | 251 |

Method I:

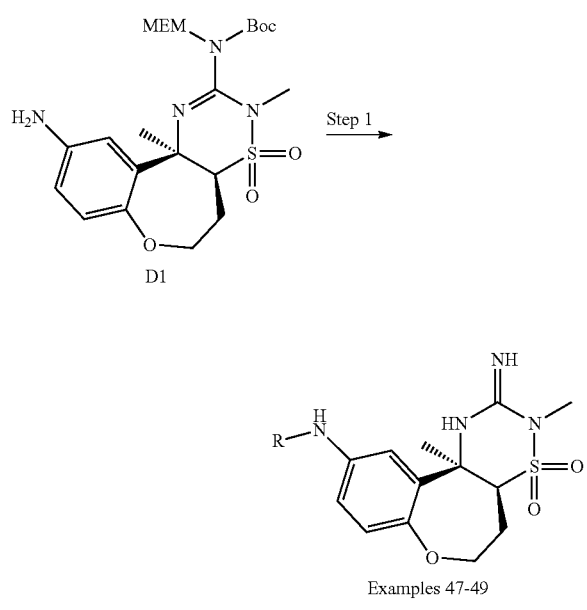

To a set of microwave vials each containing the requisite aldehyde or ketone (0.060 mmol) was added a solution of D1 (30 mg, 0.060 mmol) in CH$_2$Cl$_2$ (0.5 mL) followed by powdered 4 Å mol sieves (15 mg). The vials were capped and the mixtures were stirred at RT for 1 hr. After that time, sodium triacetoxyborohydride (19 mg, 0.090 mmol) was added and the mixtures were stirred at RT overnight. The reaction mixtures were then diluted with CH$_2$Cl$_2$ (4 mL) and filtered. The filtrate was then washed with water and the solvent was removed in vacuo. To each reaction mixture was then added TFA (1 mL) and water (0.05 mL). The mixtures were then stirred at 50° C. overnight. The solvent was removed in vacuo then the crude residues were dissolved in DMSO (1 mL) and filtered. The crude products were purified by mass triggered SFC using the following conditions: [column: Waters XBridge C18, 5 μm, 19×100 mm; solvent: gradient range 15-20% initial to 45% final MeCN (0.1% NH$_4$OH) in water (0.1% NH$_4$OH) 25 mL/min; 12-20 min run time] to afford Examples 47-49.

| Ex | Structure IUPAC Name | LCMS m/z | BACE-1 $K_i$ (nM) | BACE-2 $K_i$ (nM) |
|---|---|---|---|---|
| 47 | (4aS,11bR)-10-(cyclopentylamino)-2-imino-3,11b-dimethyl-2,3,4a,5,6,11b-hexahydro-1H-benzo[2,3]oxepino[4,5-e][1,2,4]thiadiazine 4,4-dioxide | 379.10 | 348 | 716 |
| 48 | (4aS,11bR)-10-((cyclopropylmethyl)amino)-2-imino-3,11b-dimethyl-2,3,4a,5,6,11b-hexahydro-1H-benzo[2,3]oxepino[4,5-e][1,2,4]thiadiazine 4,4-dioxide | 365.07 | 880 | 2013 |
| 49 | (4aS,11bR)-2-imino-3,11b-dimethyl-10-(propylamino)-2,3,4a,5,6,11b-hexahydro-1H-benzo[2,3]oxepino[4,5-e][1,2,4]thiadiazine 4,4-dioxide | 353.06 | 918 | 1976 |

Assays

Protocols used to determine the recited potency values for the compounds of the invention are described below.

BACE1 HTRF FRET Assay

Reagents:

Na$^+$-Acetate pH 5.0; 1% Brij-35; Glycerol; Dimethyl Sulfoxide (DMSO); Recombinant human soluble BACE1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine IC$_{50}$ values for inhibitors of the soluble human BACE1 catalytic domain. This assay monitors the increase of 620 nm fluorescence that resulted from BACE1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE1 enzyme. Inhibition of BACE1 cleavage of the QSY7-APP$^{swe}$-Eu substrate by inhibitors is manifested as a suppression of 620 nm fluorescence.

Varying concentrations of inhibitors at 3× the final desired concentration in a volume of 10 ul are preincubated with purified human BACE1 catalytic domain (3 nM in 10 μl) for 30 minutes at 30° C. in reaction buffer containing 20 mM Na-Acetate pH 5.0, 10% glycerol, 0.1% Brij-35 and 7.5% DSMO. Reactions are initiated by addition of 10 μl of 600 nM QSY7-APP$^{swe}$-Eu substrate (200 nM final) to give a final reaction volume of 30 μl in a 384 well Nunc HTRF plate. The reactions are incubated at 30° C. for 1.5 hours. The 620 nm fluorescence is then read on a Rubystar HTRF plate reader (BMG Labtechnologies) using a 50 millisecond delay followed by a 400 millisecond acquisition time window. Inhibitor IC$_{50}$ values are derived from non-linear regression analysis of concentration response curves. K$_i$ values are then calculated from IC$_{50}$ values using the Cheng-Prusoff equation using a previously determined μm value of 8 μM for the QSY7-APP$^{swe}$-Eu substrate at BACE1. Observed K$_i$ values for the non-limiting examples are reported in the tables above.

BACE-2 Assay

Inhibitor IC$_{50s}$ at purified human autoBACE-2 are determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light. Inhibitor compounds, prepared at 3× the desired final concentration in 1×BACE assay buffer (20 mM sodium acetate pH 5.0, 10% glycerol, 0.1% Brij-35) supplemented with 7.5% DMSO are preincubated with an equal volume of autoBACE-2 enzyme diluted in 1×BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, $K_m$=8 μM for 4 M for autoBACE-2) prepared in 1×BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 μs delay on a RUBYstar HTRF plate reader (BMG Labtechnologies). Raw RFU data is normalized to maximum (1.0 nM BACE/DMSO) and minimum (no enzyme/DMSO) RFU values. $IC_{50s}$ are determined by nonlinear regression analysis (sigmoidal dose response, variable slope) of percent inhibition data with minimum and maximum values set to 0 and 100 percent respectively. Similar $IC_{50s}$ are obtained when using raw RFU data. The $K_i$ values are calculated from the $IC_{50}$ using the Cheng-Prusoff equation.

We claim:
1. A compound, or a pharmaceutically acceptable salt thereof, said compound having the structural Formula (I):

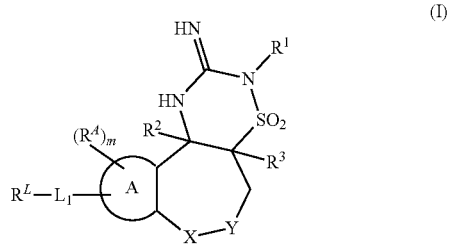

or a tautomer thereof having the structural Formula (I'):

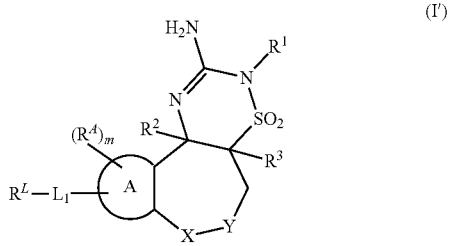

or pharmaceutically acceptable salt thereof, wherein:
-$L_1$- is a divalent moiety selected from the group consisting of —C(O)NH—, —CH$_2$C(O)NH—, —NH—, —CH(CH$_3$)NH— and —CH$_2$NH—;
$R^1$ is selected from the group consisting of H, alkyl, cycloalkyl, and -alkyl-cycloalkyl,
   wherein each said alkyl, cycloalkyl, and -alkyl-cycloalkyl, is optionally substituted with one or more halogen, and
   wherein 1 to 2 non-adjacent, non-terminal carbon atoms in said alkyl are optionally independently replaced with —O—, —NH—, —N(alkyl)-, —S—, —S(O)—, or —S(O)$_2$—;
$R^2$ is selected from the group consisting of H, alkyl, cycloalkyl, -alkyl-cycloalkyl, heterocycloalkyl, and -alkyl-heterocycloalkyl,
   wherein each said alkyl, cycloalkyl, -alkyl-cycloalkyl, heterocycloalkyl, and -alkyl-heterocycloalkyl is optionally substituted with one or more halogen, and
   wherein 1 to 2 non-adjacent, non-terminal carbon atoms in said alkyl are optionally independently replaced with —O—, —NH—, —N(alkyl)-, —S—, —S(O)—, or —S(O)$_2$—;
$R^3$ is selected from the group consisting of H, halogen, alkyl, cycloalkyl, and -alkyl-cycloalkyl,
   wherein said alkyl, cycloalkyl, and -alkyl-cycloalkyl are optionally substituted with one or more fluorine, and
   wherein 1 to 2 non-adjacent, non-terminal carbon atoms in said alkyl are optionally independently replaced with —O—, —NH—, or —N(alkyl)-;
X is selected from the group consisting of —C(R$^{4X}$)$_2$—, —O—, —S—, —S(O)—, and —S(O)$_2$—, and Y is C(R$^{4Y}$)$_2$—,
or, alternatively, X is C(R$^{4X}$)$_2$— and Y is selected from the group consisting of —C(R$^{4Y}$)$_2$—, —O—, —S—, —S(O)—, and —S(O)$_2$—;
each R$^{4X}$, when present, is independently selected from the group consisting of H, halogen, alkyl, and cycloalkyl,
   wherein said alkyl and cycloalkyl are each optionally independently unsubstituted or substituted with one or more halogen, and
   wherein 1 to 2 non-adjacent, non-terminal carbon atoms in said alkyl are optionally independently replaced with —O—, —NH—, —N(alkyl)-, —S—, —S(O)—, or —S(O)$_2$—;
each R$^{4Y}$, when present, is independently selected from the group consisting of H, halogen, alkyl, and cycloalkyl,
   wherein said alkyl and cycloalkyl are each optionally independently unsubstituted or substituted with one or more halogen, and
   wherein 1 to 2 non-adjacent, non-terminal carbon atoms in said alkyl are optionally independently replaced with —O—, —NH—, —N(alkyl)-, —S—, —S(O)—, or —S(O)$_2$—;
ring A is selected from the group consisting of aryl and heteroaryl;
m is 0 or more, with the proviso that the value of m does not exceed the number of available substitutable hydrogen atoms on ring A;
each R$^A$, when present, is independently selected from the group consisting of halogen, oxo, —OH, —CN, alkyl, —O-alkyl, and cycloalkyl,
   wherein said alkyl, —O-alkyl, and cycloalkyl of R$^A$ are each optionally independently unsubstituted or substituted with one or more fluorine, and
   wherein 1 to 2 non-adjacent, non-terminal carbon atoms in said alkyl are optionally independently replaced with —O—, —NH—, —N(alkyl)-, —S—, —S(O)—, or —S(O)$_2$—;
$R^L$ is selected from the group consisting of H and alkyl,
   wherein said alkyl of $R^L$ are each optionally unsubstituted or substituted with one or more halogen, and
   wherein 1 to 2 non-adjacent, non-terminal carbon atoms in said alkyl are optionally independently replaced with —O—, —NH—, —N(alkyl)-, —S—, —S(O)—, or —S(O)$_2$—;

or, alternatively, $R^L$ is a moiety having the formula

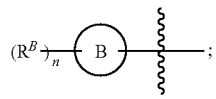

wherein
ring B is selected from the group consisting of aryl, heteroaryl, cycloalkyl, and heterocycloalkyl;
n is 0 or more, with the proviso that the value of n does not exceed the number of available substitutable hydrogen atoms on ring B; and
each $R^B$, when present, is independently selected from the group consisting of halogen, oxo, —OH, —CN, —SF$_5$, —OSF$_5$, —OR$^{5B}$, —SR$^{5B}$, alkyl, alkenyl, alkynyl, cycloalkyl, -alkyl-cycloalkyl, heterocycloalkyl, -alkyl-heterocycloalkyl, aryl, and heteroaryl,
wherein said alkyl, alkenyl, alkynyl, cycloalkyl, -alkyl-cycloalkyl, heterocycloalkyl, -alkyl-heterocycloalkyl, aryl, and heteroaryl of $R^B$ are each optionally independently unsubstituted or substituted with one or more groups independently selected from $R^6$, and;
wherein 1 to 2 non-adjacent, non-terminal carbon atoms in said alkyl are optionally independently replaced with —O—, —NH—, —N(alkyl)-, —S—, —S(O)—, or —S(O)$_2$—
each $R^{5B}$, when present, is independently selected from the group consisting of alkyl, alkenyl, alkynyl, cycloalkyl, -alkyl-cycloalkyl, heterocycloalkyl, -alkyl-heterocycloalkyl,
wherein each said alkyl, alkenyl, alkynyl, cycloalkyl, -alkyl-cycloalkyl, heterocycloalkyl, -alkyl-heterocycloalkyl of $R^{5B}$ is unsubstituted or optionally substituted with one or more fluorine, and
wherein 1 to 2 non-adjacent, non-terminal carbon atoms in said alkyl are optionally independently replaced with —O—, —NH—, —N(alkyl)-, —S—, —S(O)—, or —S(O)$_2$—; and
each $R^6$, when present, is independently selected from the group consisting of halogen, —OH, —CN, alkyl, alkoxy, cycloalkyl, -alkyl-cycloalkyl, —O-cycloalkyl, heterocycloalkyl, and -alkyl-heterocycloalkyl,
wherein each said alkyl, alkoxy, cycloalkyl, -alkyl-cycloalkyl, —O-cycloalkyl, heterocycloalkyl, and -alkyl-heterocycloalkyl are optionally substituted with one or more fluorine, and
wherein 1 to 2 non-adjacent, non-terminal carbon atoms in said alkyl are optionally independently replaced with —O—, —NH—, —N(alkyl)-, —S—, —S(O)—, or —S(O)$_2$—.

2. A compound of claim 1, or a tautomer thereof, or a pharmaceutically acceptable salt of said compound or said tautomer, wherein:
$R^1$ is selected from the group consisting of H, methyl, ethyl, cyclopropyl, —CH$_2$-cyclopropyl, and —CH$_2$CH$_2$OCH$_3$;
$R^2$ is selected from the group consisting of H, methyl, ethyl, cyclopropyl, —CH$_2$-cyclopropyl, —CH$_2$F, —CHF$_2$, —CF$_3$, and —CH$_2$OCH$_3$; and
$R^3$ is selected from the group consisting of H, fluoro, chloro, methyl, ethyl, cyclopropyl, —CH$_2$-cyclopropyl, —CH$_2$OCH$_3$.

3. A compound of claim 2, or a tautomer thereof, or a pharmaceutically acceptable salt of said compound or said tautomer, wherein:
X is —C(R$^{4X}$)$_2$—; and
Y is —C(R$^{4Y}$)$_2$—.

4. A compound of claim 2, or a tautomer thereof, or a pharmaceutically acceptable salt of said compound or said tautomer, wherein:
X is —O—; and
Y is —C(R$^{4Y}$)$_2$—.

5. A compound according to claim 1, or a tautomer thereof, or a pharmaceutically acceptable salt of said compound or said tautomer, wherein:
ring A is selected from the group consisting of phenyl, pyridazinyl, pyridyl, pyrimidinyl, pyrazinyl, pyrazolyl, triazinyl, thiazolyl, and thienyl;
m is 0 or more, with the proviso that the value of m does not exceed the number of available substitutable hydrogen atoms on ring A;
and each $R^A$ group, when present, is independently selected from the group consisting of fluoro, chloro, bromo, —CN, —OCH$_3$, —CH$_2$OCH$_3$, methyl, ethyl, cyclopropyl, —CF$_3$, —CHF$_2$, —CH$_2$F, —OCF$_3$, and —OCHF$_2$.

6. A compound of claim 5, or a tautomer thereof, or a pharmaceutically acceptable salt of said compound or said tautomer, wherein:
$L^1$ is —C(O)NH—; and
$R^L$ is a moiety having the formula

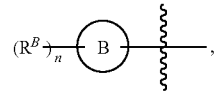

wherein:
ring B is selected from the group consisting of indolyl, isothiazolyl, isoxazolyl, oxadiazolyl, oxazolyl, phenyl, pyrazinyl, pyrazolyl, pyridazinyl, pyridyl, pyrimidinyl, pyrrolyl, thiadiazolyl, thiazolyl, and thienyl;
n is 0, 1, or 2; and
each $R^B$ group, when present, is independently selected from the group consisting of fluoro, chloro, bromo, —CN, —OCH$_3$, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —C≡CH, —C≡C—CH$_3$, —CF$_3$, —CHF$_2$, —OCF$_3$, and —OCHF$_2$.

7. A compound of claim 5, or a tautomer thereof, or a pharmaceutically acceptable salt of said compound or said tautomer, wherein:
$L_1$ is —NH—; and
$R^L$ is a moiety having the formula

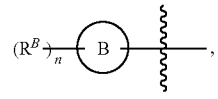

wherein:
ring B is selected from the group consisting of cyclopentyl, phenyl, pyridinyl, pyrimidinyl, naphthyridinyl, pyridopyrimidinyl, pyridopyrazinyl, and pteridinyl;

n is 0, 1, or 2; and each $R^B$ group, when present, is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —C≡CH, —C≡C—CH$_3$, —CF$_3$, —CHF$_2$, —OCF$_3$, and —OCHF$_2$.

8. A compound of claim 5, or a tautomer thereof, or a pharmaceutically acceptable salt of said compound or said tautomer, wherein:

$L^1$ is —CH$_2$NH—; and $R^L$ is a moiety having the formula

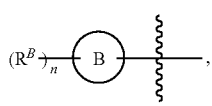

wherein:

ring B is selected from the group consisting of cyclobutyl, cyclopropyl, phenyl, pyrazinyl, and pyridyl;

n is 0, 1, or 2; and each $R^B$ group, when present, is independently selected from the group consisting of fluoro, chloro, bromo, —CN, —OCH$_3$, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —C≡CH, —C≡C—CH$_3$, —CF$_3$, —CHF$_2$, —OCF$_3$, and —OCHF$_2$.

9. A compound of claim 1, or a tautomer thereof, or a pharmaceutically acceptable salt of said compound or said tautomer, said compound selected from the group consisting of:

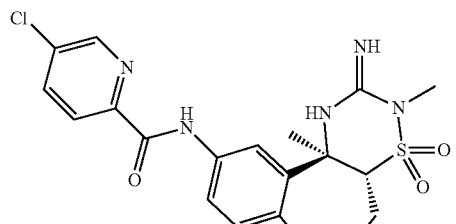

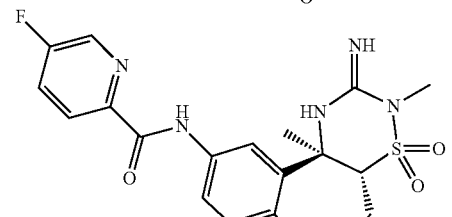

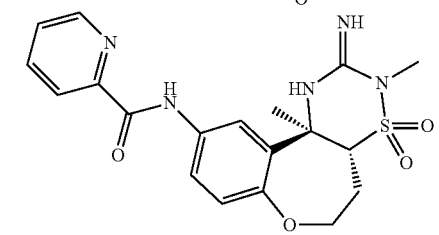

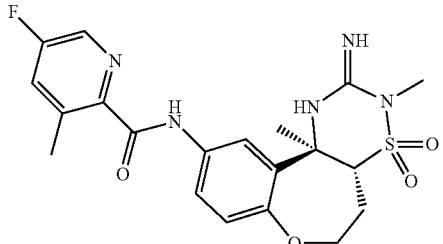

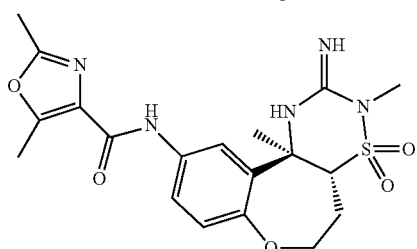

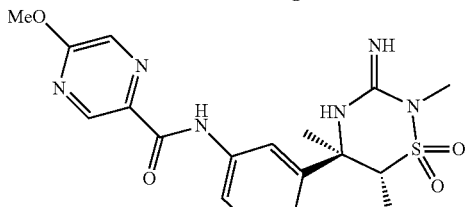

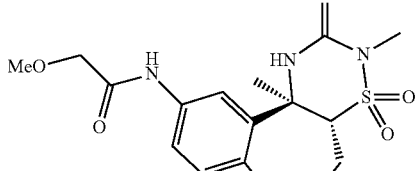

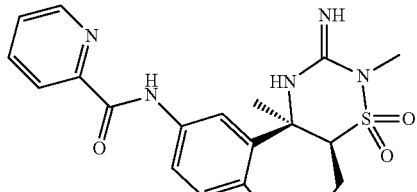

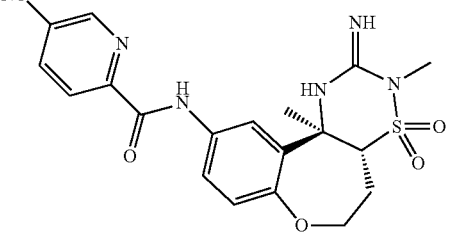

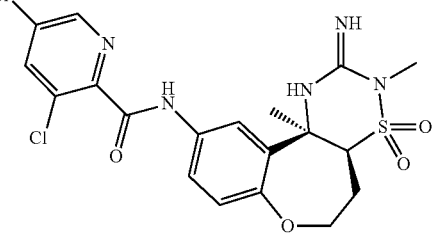

81
-continued
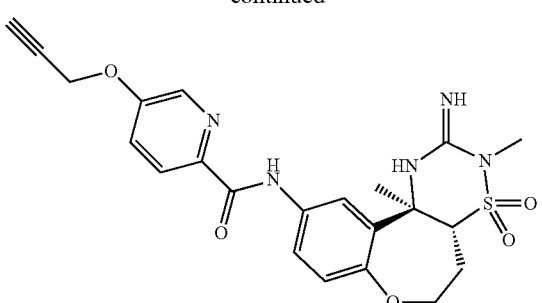
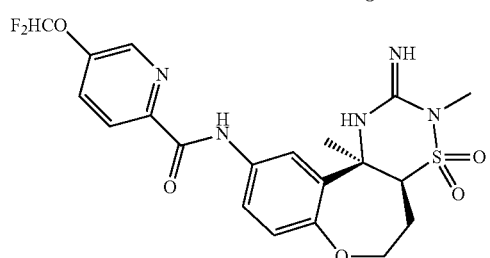
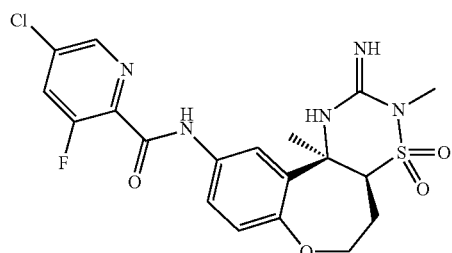
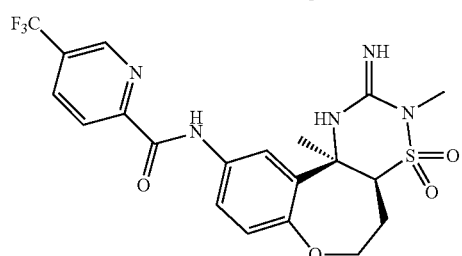
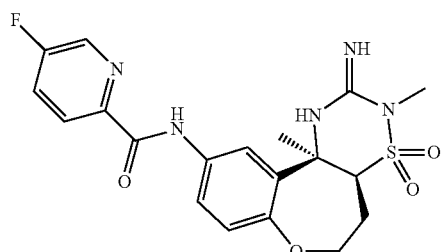
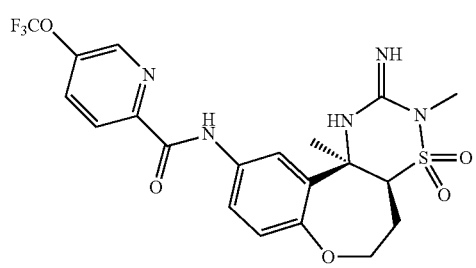
82
-continued
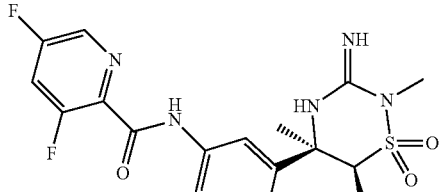
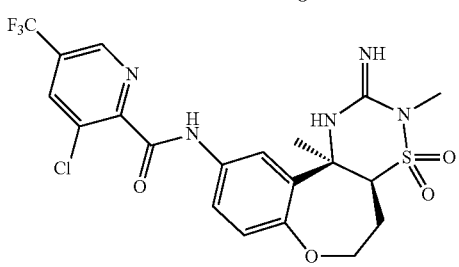
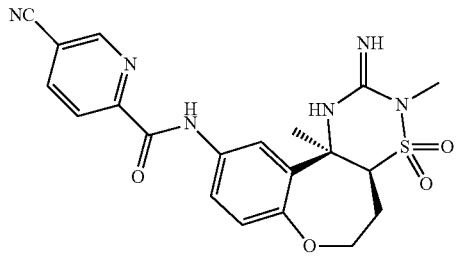
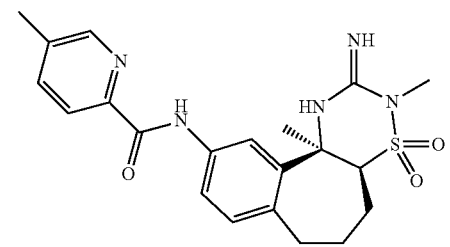
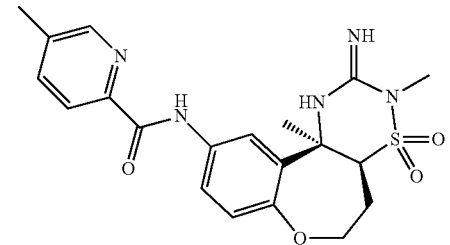
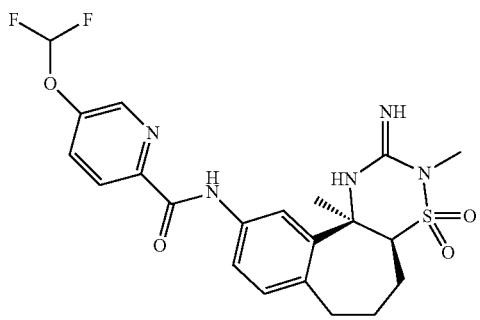

83
-continued
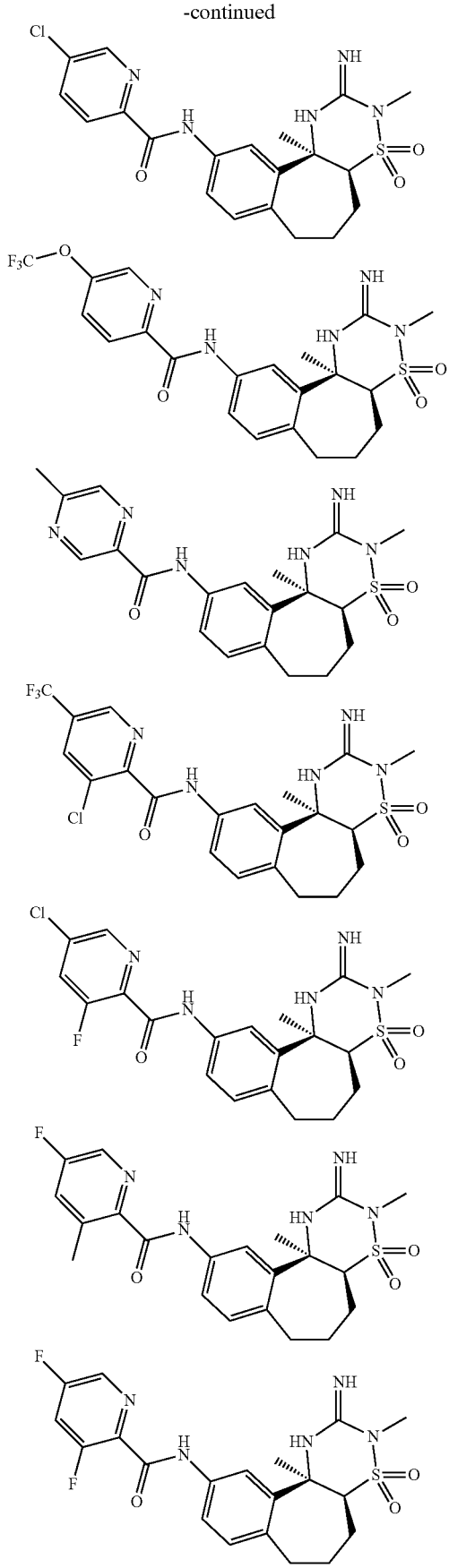
84
-continued
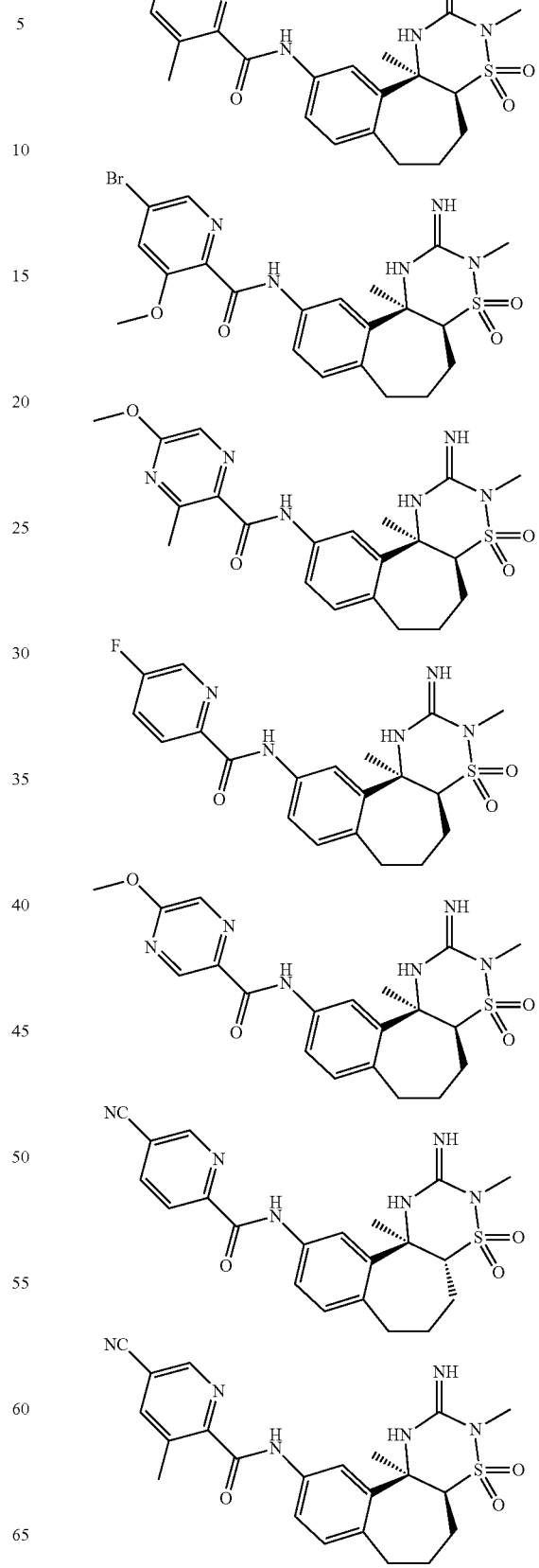

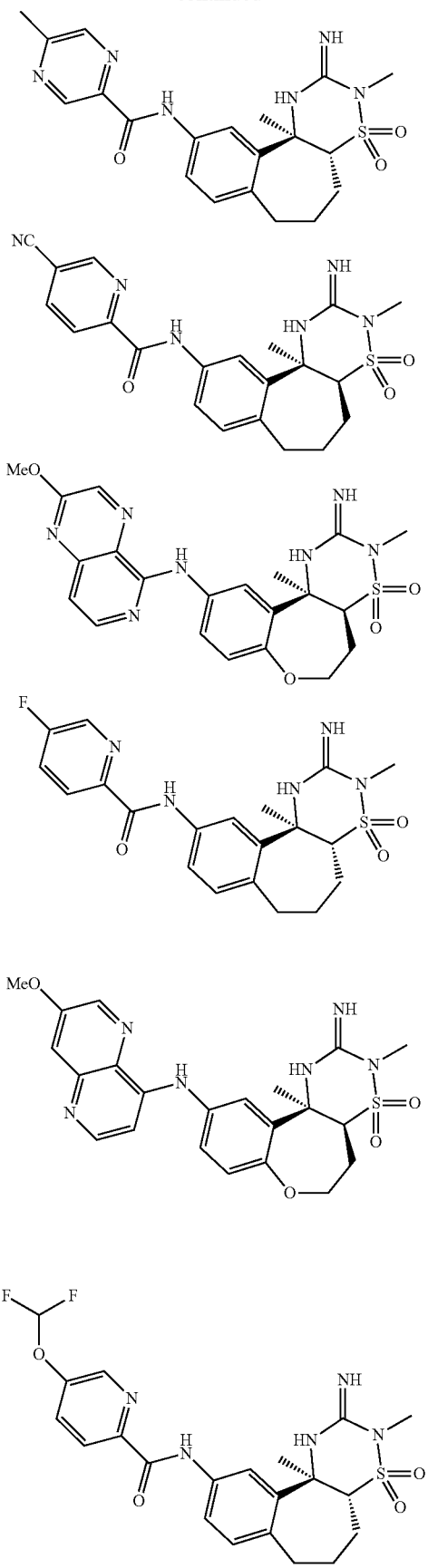
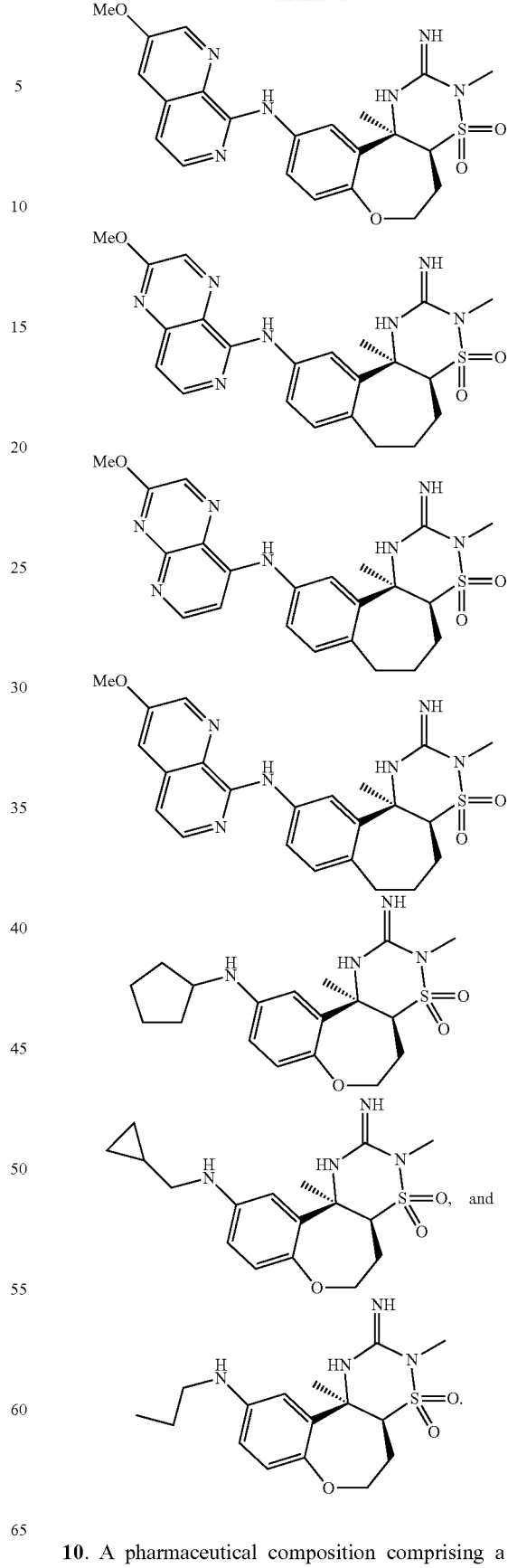
10. A pharmaceutical composition comprising a compound according to claim 1, or a tautomer thereof, or a pharmaceutically acceptable salt of said compound or said tautomer, and a pharmaceutically acceptable carrier or diluent.

11. A method of treating Alzheimer's disease, said method comprising administering an effective amount of a compound according to claim 1, or a tautomer thereof, or a pharmaceutically acceptable salt of said compound or said tautomer, to a patient in need thereof.

* * * * *